United States Patent [19]

Knispel et al.

[11] Patent Number: 4,883,067

[45] Date of Patent: Nov. 28, 1989

[54] METHOD AND APPARATUS FOR TRANSLATING THE EEG INTO MUSIC TO INDUCE AND CONTROL VARIOUS PSYCHOLOGICAL AND PHYSIOLOGICAL STATES AND TO CONTROL A MUSICAL INSTRUMENT

[75] Inventors: Joel Knispel, Timonium; Geoffrey Wright, Baltimore, both of Md.

[73] Assignee: Neurosonics, Inc., Baltimore, Md.

[21] Appl. No.: 49,992

[22] Filed: May 15, 1987

[51] Int. Cl.⁴ .............................................. A61B 5/04
[52] U.S. Cl. ...................................... 128/732; 600/28
[58] Field of Search ............................... 128/731-733, 128/1 C, 905; 84/1.24-1.27

[56] References Cited

U.S. PATENT DOCUMENTS

| | | | |
|---|---|---|---|
| 3,699,234 | 10/1972 | Adachi | 84/1.24 |
| 3,705,948 | 12/1972 | Tomisawa | 84/1.24 |
| 3,753,433 | 8/1973 | Bakerich et al. | 128/732 |
| 3,821,949 | 7/1974 | Hartzell | 128/732 |
| 3,837,331 | 9/1974 | Ross | 128/905 X |
| 3,855,998 | 12/1974 | Hidalgo-Briceno | 128/732 |
| 3,882,850 | 5/1975 | Bailin | 128/732 |
| 3,884,218 | 5/1975 | Monroe | 128/1 C |
| 3,978,847 | 9/1976 | Fehmi et al. | 128/732 |
| 4,031,883 | 6/1977 | Fehmi et al. | 128/732 |
| 4,126,125 | 11/1978 | Agoston | 128/732 |
| 4,141,344 | 2/1979 | Barbara | 128/1 C |
| 4,228,807 | 10/1980 | Yagi et al. | 128/732 |
| 4,275,744 | 6/1981 | Thornton | 128/731 |
| 4,289,121 | 9/1981 | Kupriyanovich | 128/1 C |
| 4,334,545 | 6/1982 | Shiga | 128/731 |
| 4,335,710 | 6/1982 | Williamson | 128/1 C |
| 4,354,505 | 10/1982 | Shiga | 128/732 |
| 4,407,299 | 10/1983 | Culver | 128/732 |
| 4,454,886 | 6/1984 | Lee | 128/715 |
| 4,462,411 | 7/1984 | Richards | 128/746 |
| 4,493,327 | 1/1985 | Bergelson et al. | 128/731 |

OTHER PUBLICATIONS

*Baltimore Magazine*, May 1986, "Music of the Hemispheres".

*The Peabody*, "Electronic and Computer Music at the Peabody Conservatory", Geoffrey Wright, presented at the International Computer Music Conference, 21 Aug. 1985, Vancouver, B.C.

*The Baltimore Sun*, Feb. 14, 1986, "Music From the Mind".

The Johns Hopkins University Gazette, Mar. 11, 1986, "New Field of Psychoacoustics Melds Music and Medicine".

*Johns Hopkins Magazine*, Apr. 1986, "Brain Waves Make Music-Literally".

(List continued on next page.)

Primary Examiner—Edward M. Coven
Assistant Examiner—Angela D. Sykes
Attorney, Agent, or Firm—Bacon & Thomas

[57] ABSTRACT

A method and apparatus for applying a musical feedback signal to the human brain, or any other brain, to induce controllable psychological and physiological responses. A signal representing the ongoing electroencephalographic (EEG) signal of a brain preferably is obtained from the electrode location on the scalp known as CZ or P3 in clinical notation. A signal processor converts the ongoing EEG into electrical signals which are converted into music by synthesizers. The music is acoustically fed back to the brain after a time delay calculated to shift the phase of the feedback in order to reinforce specific or desired ongoing EEG activity from the scalp position of interest. The music is comprised of at least one voice that follows the moment-by-moment contour of the EEG in real time to reinforce the desired EEG activity. The music drives the brain into resonance with the music to provide a closed loop or physiological feedback effect. Preferably, the musical feedback comprises additional voices that embody psychoacoustic principles as well as provide the content and direction normally supplied by the therapist in conventional biofeedback. The invention contemplates numerous applications for the results obtained.

71 Claims, 9 Drawing Sheets

OTHER PUBLICATIONS

*The Evening Sun,* May 14, 1982, "Art, Psychology Meet in Wave Music".
*Fort Lauderdale News,* May 14, 1982, "This 'New Wave' Comes From the Brain".
*Business Week,* Jul. 8, 1985, "Racking the Brain to Create 'Live' Stereo Sound".
*The Post,* May 14, 1982, "Art, Psychology Meet in Brain Wave Music".
*The Banner,* May 13, 1982, "Music (?) Tapped from Brain".
*The Times,* May 1982, "Scientific Music Researcher Finds New Wave in Brain Waves".
Purchase Order from Eastman Kodak Company, Rochester, N.Y. to Dr. Joel Knispel, dated Jul. 12, 1982, with Statement describing Job/Services.
*The News,* May 13, 1982, "Art, Psychology Meet in Brain Wave Music".

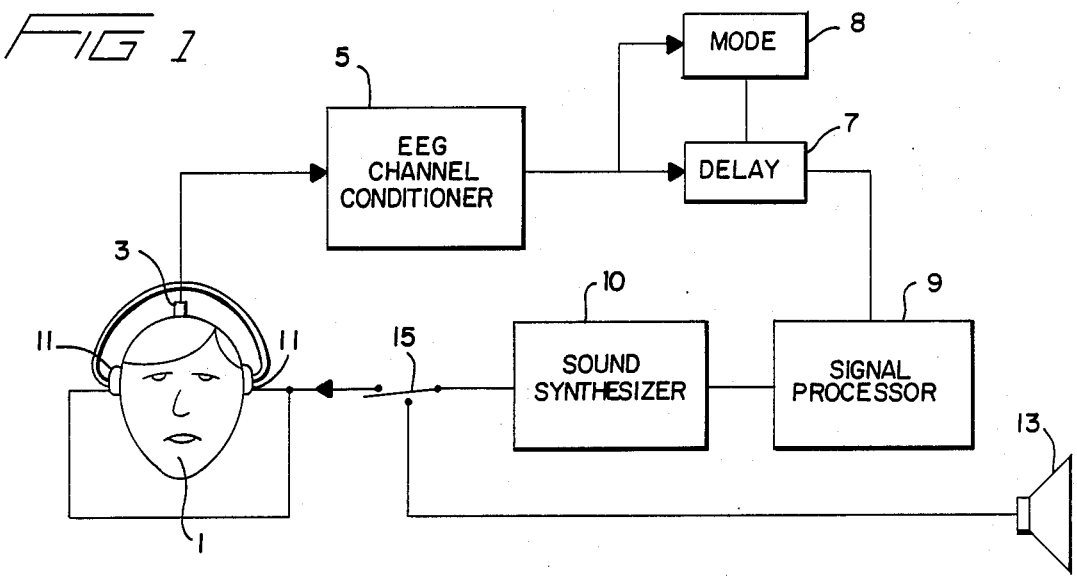
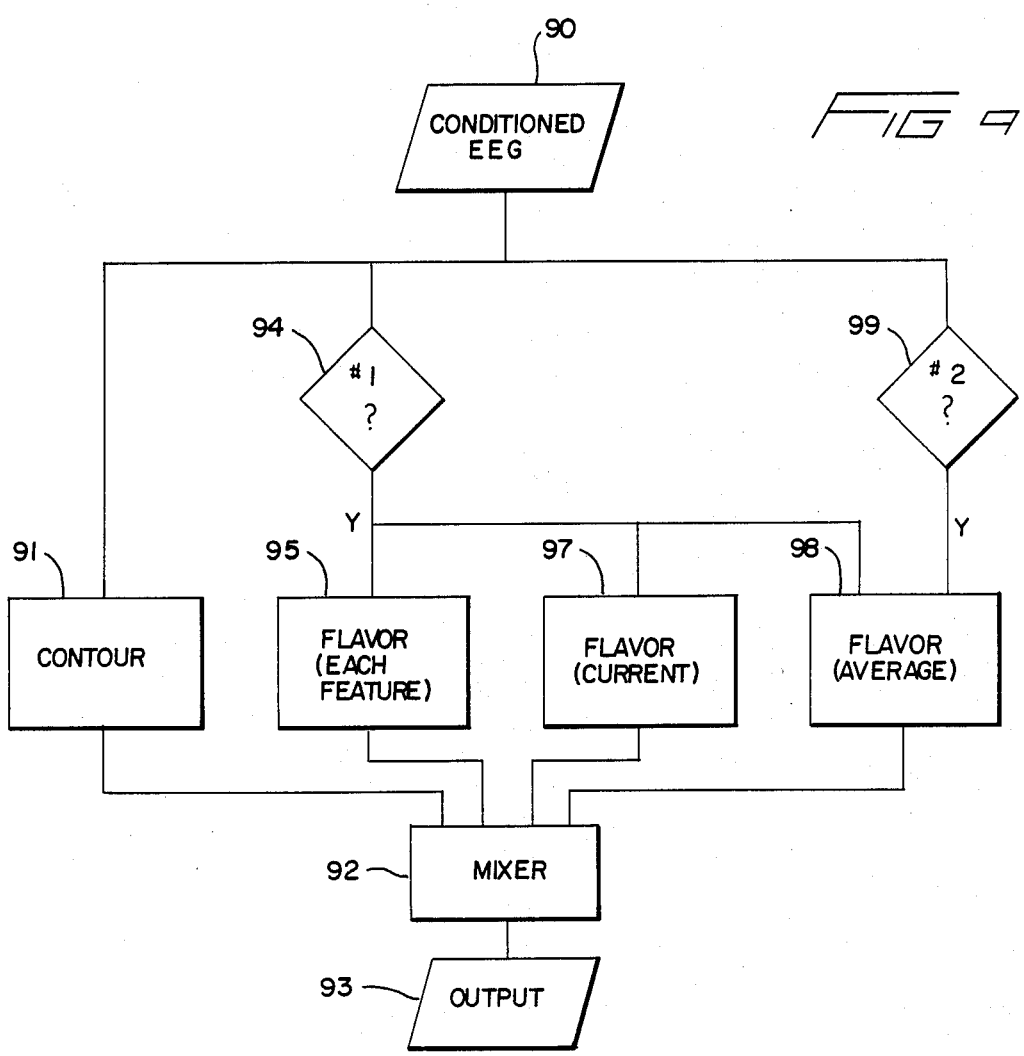

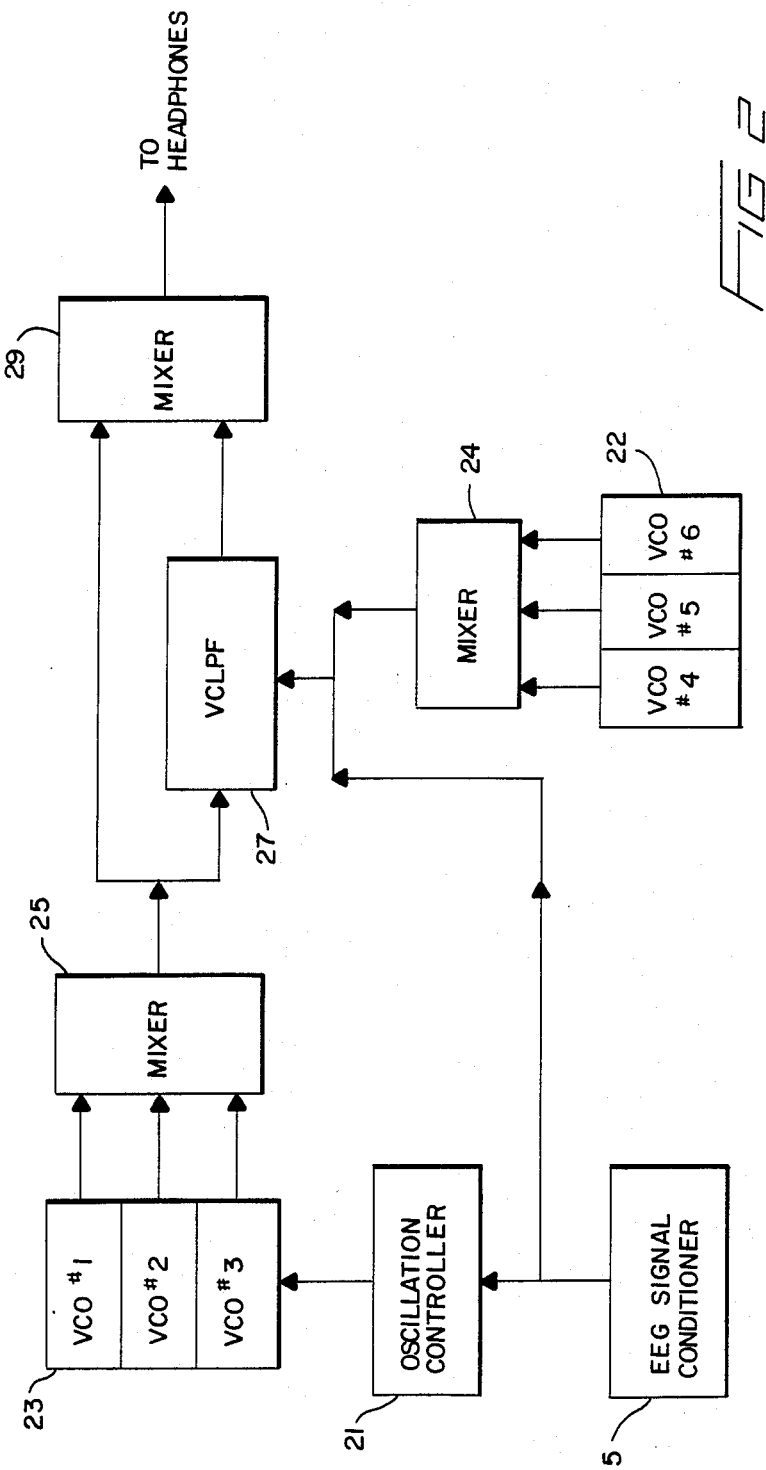

4,883,067

METHOD AND APPARATUS FOR TRANSLATING THE EEG INTO MUSIC TO INDUCE AND CONTROL VARIOUS PSYCHOLOGICAL AND PHYSIOLOGICAL STATES AND TO CONTROL A MUSICAL INSTRUMENT

BACKGROUND OF THE INVENTION

1. Field of Invention

The present invention relates to the general field of psychoacoustics which is defined, for purposes of this application, as the neuropsychological response of the brain to music. Specifically, the invention relates to a method and apparatus for translating an electroencephalographic (EEG) signal into specifically engineered music, feeding back that music to a selected area of the brain, via the ear, from which the EEG signal was generated so as to induce and control a wide variety of psychological and physiological states. The invention uses a new type of biofeedback music. The principles controlling the generation of this biofeedback are henceforth known as neuroacoustics.

2. Description of related knowledge

The human brain exhibits periodic electrical activity, also known as brain waves, at the microvolt level in discrete frequency ranges. This brain wave activity has traditionally been classified by frequency as follows: alpha waves lie in the frequency range of 8 to 13 Hz, beta waves lie in the frequency range of 13 to 28 Hz, and theta waves lie in the frequency range of 4 to 8 Hz. The brain also exhibits delta waves during sleep which are characterized by a relatively high amplitude and very low frequency, typically less than one complete cycle per second. Beta waves have a relatively low amplitude and correspond to a high level of arousal or anxiety. The brain is known to produce primarily alpha waves when a person is in a state of rest and relaxation. Theta waves are often associated with pre-sleep, dream-like mentations and visual imagery.

It is also known that EEG activity, muscular activity and other physiological measures may be modified with "biofeedback". Conventional biofeedback involves converting some measurable physiological activity of an individual into a feedback signal comprising an auditory or visual stimulus. The feedback signal provides the individual with an indication of his or her physiological activity. One type of biofeedback apparatus converts alpha waves into an audible tone that has a volume or pitch corresponding to the average level of alpha wave activity. Some individuals can alter their internal emotional state and relax by learning to alter the feedback signal.

Conventional biofeedback, however, has well known limitations. Most individuals require multiple sessions with a trained therapist to learn to adjust their brain wave activity in response to the feedback signal. Biofeedback can be tiresome and boring when the feedback signal has no interesting or pleasing qualities. Some studies have found that conventional biofeedback is so mechanistically routine that the feedback signal does not induce an effect unless a therapist is present to add emotional content and direction to the experience.

The feedback signal normally indicates only a time average of the relevant physiological activity. As such, conventional biofeedback provides an information pathway by which the brain is made consciously aware of the physiological activity. The feedback signal, however, has no direct effect on ongoing physiological activity and therefore cannot produce a true real time cybernetic feedback loop. U.S. Pat. Nos. 3,978,847 and 4,031,884 to Fehmi et al disclose a multiple channel phase integrating biofeedback computer that generates a feedback signal having a tone whose volume rises and falls with the rise and fall of the voltage in subsequent cycles of a brain wave train such as an alpha burst. The therapist or individual using the biofeedback computer may adjust a phase shift network to shift the phase of the feedback signal relative to the user's brain wave activity in accord with personal experience or personal preference. This feedback signal, however, does not appear to actively promote brain wave activity, nor does the feedback tone have musical or emotional content. Hence, the exact phase relationship of the feedback signal to the brain wave activity is not specified and does not appear to be critical to the proper functioning of the biofeedback computer.

Various approaches have been proposed to overcome the inadequacies of conventional biofeedback. One method for promoting relaxation is to play prerecorded complex sounds or colors which are at least not annoying and perhaps even psychologically enjoyable. The prerecorded sounds or colors may or may not be controlled by some measured physiological quantity. The feedback, however, does not communicate current, ongoing physiological activity, nor does the feedback induce or reinforce a physiological response. Rather, the feedback signal remains only an aid to learning which permits a person to learn to adjust his or her physiological activity.

Composers such as David Rosenboom and Alvin Lucier have incorporated EEG signals into musical compositions. These efforts have produced music that is interesting from an aesthetic perspective. The EEG signals are obtained from electrodes that are placed on the scalp without regard the physiological significance of the area of the brain that is producing the EEG activity. It is not surprising, therefore, that these musical composers have neither attained a real time physiological feedback loop nor advanced a workable methodology for attaining such an end.

Thomas Mullholland and Benard Turskey have criticized conventional biofeedback because the biofeedback signal communicates exclusively learning information. They maintain that the biofeedback signal should incorporate principles of engineering and cybernetics. Specifically, the feedback signal should be multidimensional and contain information about many features of the physiological response of interest. Further, the return of the feedback signal to the biological system of origin should be controlled so as to directly encourage and reinforce a desired physiological response. This criticism of conventional biofeedback is well taken. However, no known biofeedback device can induce a physiological response consistent with the procedural objectives proposed by Mullholland and Turskey.

Neurophysiologists know how to induce neural activity in the human brain using external stimuli. Sound is particularly useful stimulus because much of the cerebral cortex is sensitive to acoustical stimulation. Large scale neural activity may be induced in response to a variety of sounds. For example, the cortical electroencephalogram is particularly responsive to punctate sounds such as those produced by a drum or bell. The "evoked potential" phenomenon uses punctate sounds to periodically stimulate the brain. The brain eventually responds to the stimulation by producing brain wave activity at the same frequency as the stimulus. The punctate sound "drives" the brain to produce brain wave activity at the frequency selected by the neurophysiologist. A flashing light is sometimes used as an alternate form of stimulation or as a supplement to the acoustical stimulation.

The physiological stimulation associated with the evoked potential becomes unpleasant if continued for a period of time. Indeed, an evoked potential session becomes particularly unpleasant when uninteresting, regularly occurring stimuli are used to synchronously drive the EEG at a particular frequency. This unfavorable psychological response appears to result, at least in part, from the inability of the brain to control the external stimulus.

Musicians know how to give sound a form, content and direction that is both interesting and emotionally moving to a listener. Such sounds are commonly known as music. The ability of music to produce an emotional response has been known for many centuries in cultures throughout the world. Only recently, however, have psychologists and musicians begun to codify the principles that govern the emotional response to music or to exploit this knowledge with newly developed methods of precise music synthesis.

Music typically has not been used to evoke controlled responses in the brain nor has the feedback signal produced by conventional biofeedback devices been specifically organized into musical form. This is surprising since musicians know how to make sound convey many levels of meaning. The art has yet to appreciate the utility of music to induce particular, selectable forms of neural activity. This failure stems, at least in part, from a perceived dissimilarity in goals between the fields of music and psychophysiology. Further, the basic principles governing the unique neurological, physiological and emotional effects which music can induce when used systematically in a real time cybernetic biofeedback loop have no precedence in the art.

SUMMARY OF THE INVENTION

The present invention relates to a method and apparatus for translating an ongoing EEG signal into a musical feedback signal and applying the musical feedback signal to the human brain, or any other brain, to induce controllable physiological and psychological responses. A signal processor converts an ongoing EEG signal from a selected position on the scalp into electrical signals that music synthesizers convert into music. The brain receives the musical feedback after it is delayed by a period of time that is calculated so that the music reinforces specific or desired EEG activity at a particular area of the brain determined by the site of the recording electrode. In addition, the music is engineered to have psychoacoustical and musical properties that induce the brain to preferentially produce a particular type of EEG activity. The physiological response of the brain to the feedback music actively drives the ongoing EEG activity into resonance with the music to form a real time physiological feedback loop. The musical qualities and encoded physiological information of the feedback signal selectively reinforce biologically produced brain wave activity. The type of brain wave activity that is reinforced, together with the musical program in which it is encoded, can be used to promote emotional states without additional stimuli such as the presence of a therapist. For example, alpha activity can be enhanced so as to induce relaxation solely by musically reinforcing the alpha activity that is sensed by an electrode located on the scalp at the positions on the scalp known as CZ or P3 in the nomenclature of clinical neurology. Both locations, but particularly CZ, are preferred.

The feedback music comprises at least one voice for recording cortical auditory activity that follows and reinforces the real time, moment-by-moment contour of the EEG. At least one or more additional musical voices provide musical flavor that conveys psychological as well as psychoacoustical content. The term musical flavor means some component of the amplitude envelope or harmonic spectrum of the feedback music that is discrete from and compliments the sound used to communicate the moment-by-moment contour of the EEG. The musical flavor enlivens the feedback and makes it enjoyable for extended periods of listening. The additional one or more voices are more derivative of the contours of the ongoing EEG signal but are still psychoacoustically correct with respect to the type of EEG activity being reinforced. The term psychoacoustically correct as applied to acoustical stimuli in this context means music that is formulated in accordance with the principles of psychoacoustics, music theory, musicology, and the emotional psychology of music to produce a desired physiological response in the resonance feedback loop. Thus formulated, the feedback music provides the emotional content normally supplied by a therapist in conventional biofeedback as well as learning information that enables a person undergoing resonance feedback to learn to control his brain wave patterns.

At its most basic level, the present invention is a biofeedback apparatus that conveys real time physiological information to the brain in a musical context. The resonance loop should comprise at least two levels of information. The first level comprises physiological information about the moment-by-moment oscillations of the ongoing EEG signal. The physiological information can be conveyed by frequency modulating a tone or chord with the ongoing EEG signal so that the pitch of the tone varies in proportion to the amplitude of the ongoing EEG signal. The fed back periodic changes in frequency make the brain aware of its ongoing brain wave activity and actively reinforce its continuance unless the goal is to discourage the activity by adjusting the phase relationship of the feedback signal to cause destructive interference. The second level of information is musical flavor. The musical flavor may comprise independently generated, pseudorandom timbre modulation. Preferably, however, the musical flavor is also a psychoacoustically correct sound that is derived from ongoing brain wave activity such as timbre modulation produced by modulating an overtone sweep with the ongoing EEG signal.

The preferred embodiment of the present invention uses musical feedback comprising four distinct musical voices that create and sustain the physiological feedback loop The four voices constitute a hierarchy of EEG analysis. A first musical voice is formed by frequency modulating a tone chord with the ongoing EEG signal to communicate to the brain the moment-by-moment contour of the EEG. A second musical voice extracts and reinforces specific features of the ongoing EEG activity. The second voice may comprise a punctate sound that is generated in response to a major feature of the EEG such as a crest (local amplitude maxima) in a brain wave. The punctate sound has an effect on the brain that is analogous to a conventional evoked potential response but differs in being directly controlled by the brain so as to reinforce only naturally occurring EEG activity. A third voice uses timbre modulation to indicate the relative frequency of occurrence of a particular feature of the ongoing EEG signal. The third voice provides more derivative physiological information by more slowly modulating the upper octaves of an independently generated tone chord signal with an overtone sweep. Each overtone sweep lasts for a period of time that is greater than the period of the brain wave activity in question so that the timbre modulation appears to get brighter during a burst of brain wave activity. The timbre modulation thus bears some resemblance to the naturally occurring EEG activity even while being more derivative of its moment-by-moment profile. A fourth voice conveys physiological information by slowing and retriggering a note sequence in response to the amplitude of the ongoing EEG signal exceeding predetermined levels and in phase with the timbre modulation.

The interplay of the first, second, third and fourth voices establish a polyphonic music in which the four voices dynamically interact with the changing physiological state of the person generating the ongoing EEG signal. The fourth voice comprises a sequence that cycles through a series of notes in rapid succession. The rate at which the sequencer cycles and the duration of a cycle decreases in relation to the amplitude of the ongoing EEG signal. The sequencer responds to predetermined threshold levels of the amplitude of the ongoing EEG signal. Thus, the sequencer does not begin to reduce its cycling rate until the amplitude of the ongoing EEG signal exceeds a first threshold level. The sequencer starts over its sequence whenever the amplitude of the ongoing EEG signal exceeds a second, higher threshold level. The third voice, the overtone sweep, sounds only in response to the ongoing EEG signal exceeding the first threshold level. The amplitude of the timbre modulation produced by the overtone sweep is related to the number of occurrences of a predetermined feature of interest in the ongoing EEG signal. The second voice, the punctate bell sound, sounds only when the amplitude of the ongoing EEG signal exceeds the first threshold level. The pitch of the bell is proportional to the amplitude of the ongoing EEG signal. The first voice is a continuously varying frequency modulated tone chord. The four voices thus combine to give the feedback signal musical flavor in the form of a rich, constantly changing musical pattern that is psychologically enjoyable and psychoacoustically correct with respect to the physiological phenomenon being driven by the resonance loop.

The feedback signal communicates psychoacoustic information to the brain through a musical "language" based on the four musical voices forming a polyphonic hierarchy of perceptual prominence. A voice which is readily apparent to a listener is said to be in the foreground of the music. A less apparent voice which is still readily perceptible is said to be a midground voice. A voice which is not readily apparent in the perceptual field is said to be a background voice. In the preferred embodiment, the sequencer is a foreground voice in the absence of significant EEG activity. However, once the amplitude of the ongoing EEG signal exceeds the first threshold level, the prominence of the sequencer declines into the midground region where it is joined by the sounds of bells and timbre modulation. The sequencer drops into the background and the bells move into the foreground as the amplitude of the ongoing EEG signal increases even further. The timbre modulation remains a midground voice and follows the bell sound as "ghost" sound that adds a natural harmonic content to the feedback music. The frequency modulated tone chord remains in the background of the perceptual field as a constantly changing, ever present voice. The frequency modulation, however, is phase locked with the bell sound so that both voices reinforce ongoing EEG activity in the brain.

The perceptual hierarchy is consistent with the elements of complex musical structure advanced by Shenker, Lerdahl and Jackendoff, and others. The music, however, has unique psychoacoustical properties. The brain responds to the music as an acoustical stimulus that reinforces particular physiological activity in a real time feedback loop. The musical attributes of the feed back signal keep the physiological information from becoming either boring or annoying and make the feedback psychologically emotionally acceptable for extended listing. It is to be appreciated that the four musical voices that comprise the preferred embodiment of the present invention represent a compromise between the often contradictory considerations governing the composition of music and the selection of adequate physiological stimuli that satisfy the necessary requirements for a real time feedback loop.

The character of the musical voices also may be adjusted to contain desirable psychological and musical information. For example, the notes generated by the sequencer may be tuned in a progressively more dissonant pattern. The musical quality of the acoustical feedback is then dissonant in the absence of the desired type of EEG activity but becomes musically consonant with the production of more of the desired type of EEG activity. The person undergoing resonance feedback is thus psychologically rewarded with consonant music for producing the preferred type of EEG activity. The base frequency of the first voice may be varied in accordance with individual taste to further enhance the therapeutic effect of the resonance feedback by making the music more attractive. For example, some researchers report that individuals prefer musical tunings that approximate the frequency range of their own voice. Also, the bell sound may be replaced by any number of other punctate sounds such as a drum or harp at the preference of the individual.

The four voices communicate a complex informational stimulus on the extent to which the person has entered into a desired brain state so that the person may learn to alter his physiological activity. The preferred embodiment conveys learning information about long term, time average physiological activity through the rate, retriggering, and perceived prominence of the note sequence. The other voices also contribute information to the learning process through their relative activity and perceptual prominence.

It is significant to the present invention that the learning information and psychological information need not interfere with the physiological content of the resonance feedback loop. The physiological resonance loop reinforces naturally occurring EEG activity so long as at least some of the musical voices are psychoacoustically correct and the remaining musical voices are not psychoacoustically incorrect in the sense of producing a physiological, psychological or psychoacoustical response that antagonizes the physiological resonance activity. The note sequencer is an example of a musical voice that provides only marginal direct physiological information by starting over when the ongoing EEG signal exceeds the second threshold. The note sequencer is nevertheless not inconsistent with physiological resonance since the production of each note is unrelated to the moment-by-moment activity of the ongoing EEG signal and the sequence as a whole does not interfere with the other voices. Arranging the sequence of notes in a dissonance pattern has the additional advantage of making the note sequencer a psychologically correct voice, in terms of incentive, as well as the primary conveyer of learning information.

The musical structure of the feedback signal enables a person to learn how to bring his EEG activity under volitional control. Experiments have shown that persons can learn to adjust their EEG activity in less than six minutes which is faster than commonly seen with conventional biofeedback. Indeed, it has been shown that individuals can modify their EEG activity to repeat musical patterns. These musical patterns are complex melodies which are unique to each individual. Nevertheless, the patterns constitute recognizable melodies that the individual producing the music can repeat at will. The learning information conveyed by the feedback signal permits people to literally produce music by cognitive control. Further, repeatable musical patterns could be used as control signals for instruments other than musical instruments. The present invention is therefore applicable to the field of man/machine interface.

It is to be appreciated that the feedback signal of the preferred embodiment of the present invention simultaneously conveys many levels of meaning through the real time resonance feedback loop. The hierarchical approach to forming the musical flavor provides a grammar which can be used to evoke an emotional response in accord with the principles of psychology and musicology. The feedback music provides emotional content such as normally supplied by the client-therapist interaction during conventional biofeedback.

Laboratory experiments have demonstrated that resonance feedback according to the present invention enhances the production of alpha wave activity in comparison to silence or the same feedback music played back so as not to be contingent on ongoing EEG activity. Further, increasing the intensity of resonance feedback music produces more EEG activity of the desired type once the level exceeds a threshold of approximately 86 decibels, at present signal to noise ratios. The words "signal" and "noise" in this context mean sound that is or is not directly correlated with ongoing physiological activity, respectively. Increasing the volume of noncontingent feedback music actually blocks production of the desired EEG activity. In addition, the time delay used in the feedback loop can maximize production of brain wave activity by precisely matching the frequency at which the brain of an individual is most inclined to generate the desired EEG activity.

The frequency modulation, bell sound, overtone sweep and note sequence comprise the only four voices that have been shown in laboratory experiments to promote physiological resonance while also maintaining the desired musical form, content and direction associated with psychoacoustically correct music. These four musical voices have been chosen for the purpose of increasing alpha activity so as to induce relaxation. It is believed that other sounds can be synthesized to obtain this result as well as other physiological and psychoacoustical objectives following the principles of neuroacoustics presented in this application.

The present invention can be practiced with music synthesizers that use analog components. It is considered preferable, however, to use digital EEG analysis and sound synthesis. Such implementation should have the advantages of increased reliability and precise adjustment of tone, pitch and gain parameters automatically, as well as automatic control over delay times and EEG feature extraction. These refinements should decrease the signal to noise ratio of the feedback music and thus lower the threshold for the onset of resonance feedback. Further, the task of creating psychoacoustically correct sounds should be greatly simplified with digital implementation due to the ease with which sounds and EEG analyses can be designed, stored and tested with digital synthesizers.

The present invention has many applications. For example, the musical feedback is itself an enjoyable form of music. Additional voices may be added to the music, inside or outside the feedback loop, to create interesting effects. For example, a white noise signal may be added to produce a thunder-like dramatic effect when the amplitude of the ongoing EEG signal exceeds a preselected threshold. The invention may be used by a clinical psychologist to facilitate various therapeutic procedures such as guided imagery by enhancing or retarding particular brain states. A neurologist may use the present invention as a musically pleasing test of brain functions by introducing a controlled punctate stimulus embedded within the music, to generate an evoked potential response. Yet another possible use for the invention is to create a form of interpersonal communication where music is generated in response to the collectively produced brain activity of several individuals. Numerous other applications are considered possible.

BRIEF DESCRIPTION OF THE DRAWINGS

FIG. 1 is a block diagram of the present invention as used in conjunction with a single individual;

FIG. 2 is a block diagram of a simplified circuit arrangement for practicing the present invention;

FIG. 9 is a flowchart of the signal processing according to the preferred embodiment of the present invention such as used in the signal processing unit shown in FIGS. 4-8;

DETAILED DESCRIPTION OF THE PREFERRED EMBODIMENTS

Figure 3:
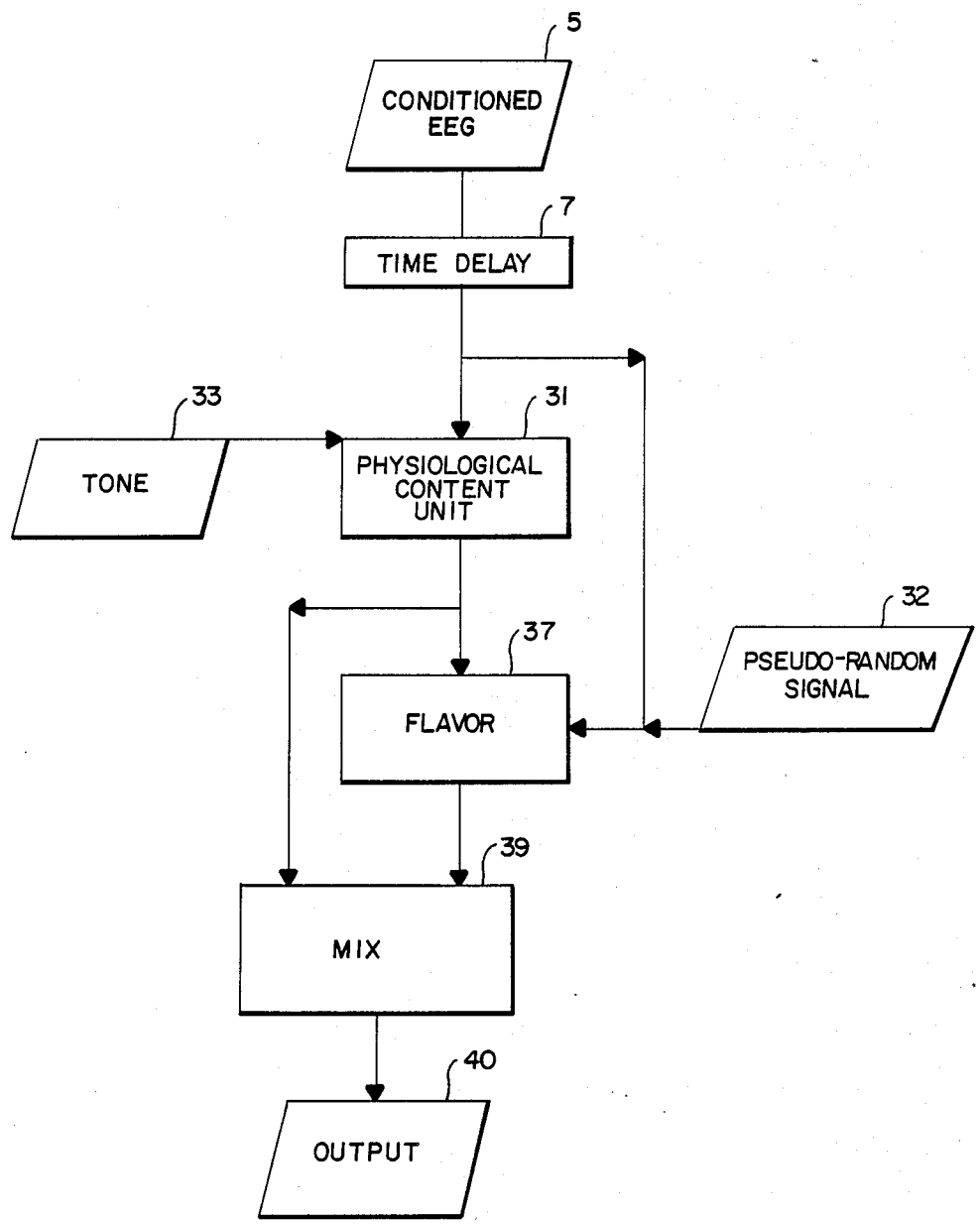
FIG. 3 is a flowchart showing the steps of signal processing used in a simplified embodiment of the invention such as the apparatus shown in FIG. 2.

FIG. 1 is a block diagram of a simplified embodiment of the present invention. An electrode 3 is applied to the scalp of a person 1. The electrode may be a variety of clinically accepted electrodes, such as a Grass gold plated EEG cup electrode. The differential recording may be either monopolar or bipolar. Using the nomenclature which is conventionally used in clinical neurology, electrode 3 is preferably located at the CZ or P3 location for reinforcing alpha activity and producing relaxation. Other locations on the scalp might be used to induce other brain states. An electroencephalograph (EEG) channel conditioner 5, comprising a Tektronix TM 503 amplifier and a Krohn-Hite 3700 filter, amplifies the EEG 10,000 to 50,000 times and filters the electrical signal from electrode 3 to produce an ongoing EEG signal, in the range of 0.5 Hz to 35 Hz, corresponding to ongoing EEG activity in the brain of the person. The ongoing EEG signal is delayed in a delay line represented by delay line 7 and discussed in detail below. An EEG analysis unit 8 determines the most probable time to the next wave form of interest and adjusts delay line 7 accordingly. An EEG signal analysis processor 9 converts the ongoing EEG signal into electrical signals from which sound synthesizer 10 can produce music. The theory and functioning of the sound synthesizer is described in detail elsewhere in this application. Headphones 11 receive output signals from sound synthesizer 10 and direct an acoustical indication of the feedback signal to the ears of the person.

Delay line 7 shifts the phase of the periodic feedback signal so that the acoustical stimulus has a predetermined phase relationship to the ongoing EEG activity occurring in the brain of the person 1. Hence, delay could occur anywhere between sensor 3 and headphones 11 such as in a a Yamaha SPX 90 digital delay located between the sound synthesizer and the headphones. To produce an appropriate phase shift, delay line 7 must compensate for the time required for the brain to process sound, the time required to analyze the EEG, the time required for the sound synthesizer to actually produce the sound, the time required for the sound to propagate through the air to the listener, and the approximate period of time to the next EEG waveform of interest. The neural conduction time from ear to auditory cortex in humans is in the range of 35 milliseconds. Thus, for example, promoting alpha wave activity typically having a period of approximately 100 milliseconds requires an additional delay in delay line 7 of approximately 65 milliseconds so that the acoustical stimulation is approximately in phase with the next alpha wave and actively reinforces the biologically produced alpha activity. Conversely, a delay of only 15 milliseconds in delay line 7 produces a total delay of 50 milliseconds so that the acoustical stimulation is shifted 90 degrees out of phase with the production of alpha wave activity. In this last instance, the acoustical feedback presumably destructively interferes with the production of alpha wave activity and thereby allows the production of other types of EEG activity associated with other brain states. Other strategies for producing destructive interference, such as reversing electrode polarity, are available.

The degree of phase shift in delay line 7 changes with the type of EEG activity being measured, location of the EEG activity, and whether and to what extent the user desires the feedback to constructively or destructively interfere with the particular form of brain wave activity. The present invention selectively encourages or discourages EEG activity associated with various behavioral states and states of consciousness by varying the period of time by which the acoustical feedback is delayed.

The EEG analysis unit 8 may comprise an analog to digital converter to convert the EEG into a digital signal and an IBM PC programmed to perform a cross point analysis on the digitized EEG signal. The cross-point analysis program may comprise counting the time required for each wave form in the ongoing EEG signal to cross a base line and then summing the number of wave forms that occur within discrete frequency ranges. The frequency range with the most occurrences is the preferred frequency of that subject. The delay line is adjusted with the inverse of the preferred frequency to approximate the period of time to the next EEG waveform. Other types of analysis other than cross point analysis such as FFT may be used. It is thought preferable to adjust the delay line on a moment-by-moment basis so that the anticipated arrival of the next brain wave corresponds to the period of the preceding brain wave.

A speaker 13, shown in FIG. 1, is connected to the output of sound synthesizer 10 by a switch 15. The speaker permits additional individuals to hear the acoustical output from the sound synthesizer. Speaker 13 may replace headphones 11 and supply feedback to person 1 if delay line 7 is adjusted to account for the longer period of time required for the sound to travel from the speaker to the person. Speaker 13 and headphones 11 should not, however, be used simultaneously unless provisions are made to prevent the acoustical output from the speaker and headphones from interfering with each other. Further, the output from sound synthesizer 10, or any other element, may be directed to additional signal processing equipment such as a recording device for subsequent editing, processing or playback.

It is to be appreciated that the present invention differs from other biofeedback or evoked potential devices by actively evoking a response with an acoustical feedback signal representing the brain's own ongoing EEG activity. The acoustical feedback actually makes the brain immediately follow its current EEG activity. Further, the physiological information encoded in the acoustical feedback signal is optimally suited to affect brain activity in desired ways because the response which the acoustical feedback induces in the brain is related to ongoing EEG activity produced by the brain itself. The utility of the present invention depends on giving the feedback sounds a form, content and direction sufficient to induce the desired response in the subject. Experiments have shown useful resonance feed back cannot be obtained without encoding the physiological information in a type of music designed in accordance with the principles of acoustics, music theory, musicology and the emotional psychology of music as explained in this application.

ABBREVIATED MODEL

FIG. 2 is a functional block diagram of an abbreviated model for converting the ongoing EEG signal into a musical feedback signal in accordance with the present invention. The abbreviated apparatus establishes physiological resonance with a minimum of musical processing and is particularly useful for quick setup and limited experimentation. Delay line 7 is omitted for simplicity of the illustration. Tone generator 23 comprises three Moog 921 B voltage controlled oscillators (VCO's), 23a, 23b and 23c respectively, having base frequencies of 75 Hz, 115 Hz and 225 Hz, respectively. The 921 B oscillators individually produce a triangular wave output signal. A Moog 921 A oscillator controller 21 determines the frequency swings of the VCO's in the proportion of a one octave increase in frequency per volt increase in the amplitude of the ongoing EEG signal from signal conditioner 5. The sensitivity of the VCO's may be adjusted by placing a Moog CP3A voltage gain/attenuator at the input from the EEG signal conditioner 5. A Moog CP3A mixer 25 combines the output from the three VCO's in the proportion of 10:6:5, respectively, so that the output signal of mixer 25 can generate a chord tone.

The output signal from mixer 25 supplies an input signal to a Moog 904A high resonant voltage control low pass filter (VCLPF) 27. The value of the voltage from the ongoing EEG signal from signal conditioner 5 modulates VCLPF 27 so that it passes the higher frequencies of the VCO's from the oscillator of mixer 25 in proportion to the amplitude of the voltage signal. In other words, the VCLPF provides mixer 29 with more of the higher frequency signals in response to more intense EEG activity. A Moog CP3A mixer 29 combines the output signals from mixer 25 and VCLPF 27 in the ratio of 1:10. The output signal from mixer 29 is converted into the acoustical feedback signal and directed to the person through headphones, not shown in FIG. 2. The musical feedback thus consists primarily of the overtone sweep generated by VCLPF 27. It is to be appreciated that the moment-by-moment oscillations in the EEG are further accentuated by maintaining the phase relationship between VCO's 23 and VCLPF 27 so that the relative strength of the higher frequency tones increases as the oscillation frequencies of the VCO's increase.

A further refinement of the invention involves adding a pseudorandom, time varying signal to the VCLPF control line so as to offset the regularity of the electronically produced sound. As shown in FIG. 2, a Moog CP3A audio mixer 24 combines the output of three Moog 921 B voltage controlled oscillators to generate an output signal from pseudorandom signal generator 22. The VCO's are adjusted to have different, relatively low frequencies of oscillation on the order of 1Hz. The VCLPF 27 combines the control signals from mixer 24 and EEG signal conditioner 5 in the ratio of 1:1.

The VCLPF 27 adds musical flavor to the output pitch from the audio frequency generator 23 in the form of timbre modulation so that the musical feedback is more pleasing to listen to over time. Modulating the timbre in proportion to, and in phase with, the ongoing EEG signal provides physiological information to the listener and is therefore effective at inducing resonance feedback. The pseudorandom voltage signal acts on the timbre or "color" of the output sound in much the same way as vibrato on an instrument such as a violin. The pseudorandom signal adds an apparent gentle rhythmic randomness to the rapid moment-by-moment oscillations of the overtone sweep and frequency modulated chord tone so as to make the timbre modulation psychologically pleasant to the listener.

FIG. 3 is a flow chart of the signal processing steps performed by the apparatus shown in FIG. 2. The ongoing EEG signal, after being amplified and filtered, forms an input at step 5 that is delayed at step 7. The time delay may occur anywhere along the signal processing path and is illustrated as occurring to the input signal so as to be consistent with FIG. 1. Physiological information is generated at physiological content step 31 by converting the moment-by-moment oscillations of the ongoing EEG signal into a signal that an audio speaker can convert into a sound to which the brain of the listener is responsive. It is psychoacoustically preferable that the physiological content step comprise a frequency modulation of the pitch of a tone chord from signal generator 33 in response to the ongoing EEG signal because the human brain is more than 30 times more sensitive to changes in pitch than changes in amplitude (loudness). Part of the output from physiological content unit 31 supplies a flavor step 37 that adds a harmonic base to the music suitable for prolonged listening. Additional flavor may be supplied by a pseudorandom signal generator 32, or the pseudorandom signal may provide the only input signal at step 37. The output from flavor step 37 and physiological content step 31 are mixed at step 39 to form an output signal at step 40 suitable for conversion into a musical feedback signal.

It is to be appreciated that the functional attributes of the flow chart shown in FIG. 3 may be implemented in a number of ways using many different apparatus, including apparatuses using the techniques of digital sound synthesis, to function in accord with the teachings of the present invention.

ENHANCED MODEL

Figure 4:
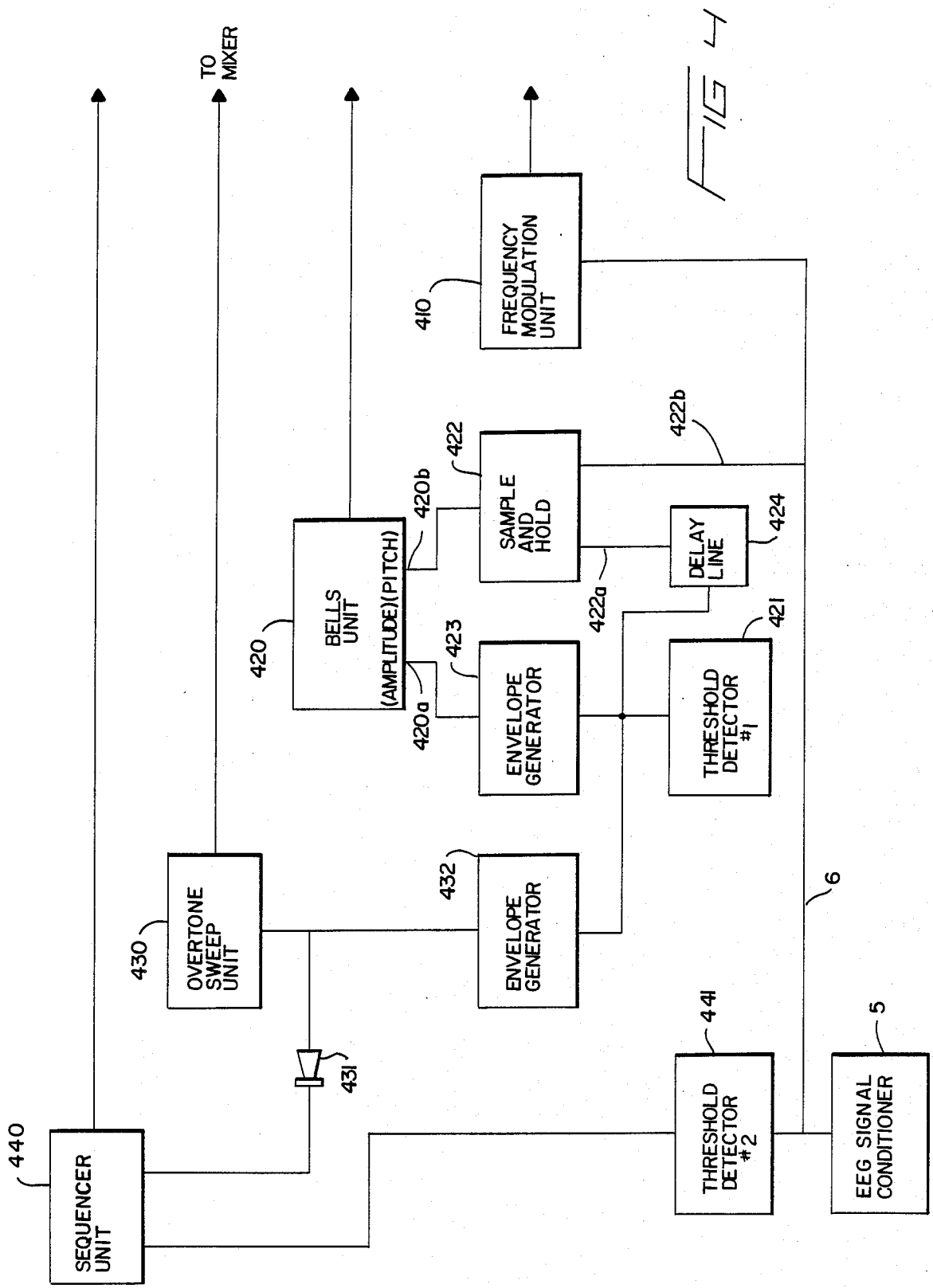
FIG. 4 is a block diagram of a signal processing unit for the preferred embodiment of the present invention.

FIG. 4 is a block diagram for an analog implementation of the preferred embodiment of the present invention. A signal bus 6 receives the ongoing EEG signal from EEG signal conditioner 5. Delay line 7 has been omitted for simplicity of illustration. Frequency modulation unit 410, bells unit 420, overtone sweep unit 430 and sequencer unit 440 convert the ongoing EEG signal on bus 6 into four signals that are mixed and converted into four musical voices through means well known in the art such as a Tascam M512 mixer, not shown in FIG. 4.

Frequency modulation unit 410 generates a tone chord that is modulated by the amplitude variations of the ongoing EEG signal. The FM unit comprises three phase locked voltage controlled oscillators tied together to form a desired harmonic relationship with other voices. The frequency modulation unit provides physiological information in the form of moment-by-moment acoustical feedback corresponding to the amplitude contour of the ongoing EEG signal on line 6, as well as a harmonic background to the complex musical superstructure formed by the other three musical voices.

Bells unit 420 generates a second voice in the form of a punctate acoustical impulse such as the sound of a struck bell. The bell unit accepts two control signal inputs, 420a and 420b, for controlling the amplitude and pitch, respectively, of the bell sound into which its output signal is ultimately converted. The occurrence of the bell is determined in relationship to the amplitude of the voltage of the ongoing EEG signal. If the EEG signal exceeds a first threshold level, a first threshold detector 421, such as a Moog 912 Schmidt trigger, supplies a voltage control signal to sample and hold unit 422 at input 422a. The sample and hold unit responds to the voltage control signal by sampling the incoming EEG and tuning a tone generator in bells unit 420.

The voltage control signal from first threshold detector 421 to sample and hold unit 422 is delayed in delay line 424 for a period of time that approximates the time required for the ongoing EEG signal to crest at a local maxima. The value of the delay time is an experimentally determined parameter, calculated for each subject, that depends on the value of the threshold level as well as the the frequency and amplitude of the ongoing EEG signal. The frequency of the tone from the tone generator is proportional to the value of the voltage at control input 422b which corresponds to the relative moment-by-moment amplitude of the ongoing EEG signal at the time that the sample and hold unit is triggered. Thus, the pitch of the tone generator is proportional to the (approximate) amplitude of the ongoing EEG signal at the crest of a brain wave.

The output from an envelope generator 423 modulates the amplitude of the signal from the bell unit so that it assumes the amplitude envelope of a bell. If the EEG signal does not exceed the first threshold level, bells unit 420 does not generate an output signal and no bell sound is produced.

Overtone sweep unit 430 generates an output signal that forms a third musical voice for the musical feedback. The overtone sweep unit comprises a plurality of tone generators. A highly resonant voltage controlled low pass filter is modulated with respect to the ongoing EEG signal so as to pass more high frequency tones in response to a greater amplitude in the ongoing EEG signal. The overtone sweep is triggered only in response to the amplitude of the ongoing EEG signal exceeding the first threshold level as indicated by a signal from envelope generator 432. Envelope generator 432 is constructed with a slow attack so that the maximum timbre modulation occurs after the sound of the bell. The timbre modulation thus serves as a "ghost" sound to the bells which adds psychoacoustically correct flavor to the music of the feedback signal.

Further, the envelope generator preferably does not completely shut off immediately after the ongoing EEG signal drops below the first threshold level. This hysteresis causes the amplitude of the output of the envelope generator to increase with increasing frequency of occurrence of brain waves that have an amplitude greater than the first threshold level. Thus, the overtone sweep produces a feedback signal that is more derivative of the ongoing EEG signal while still maintaining some correspondence with the physiological information contained in the EEG.

The output signal from sequencer unit 440 forms a fourth musical voice for the musical feedback. The sequencer can generate twenty-four notes in sequence. The sequencer receives two control signals from the ongoing EEG signal. One control signal which controls the rate at which the sequencer cycles through its sequence corresponds to the negative of the output of envelope generator 432 by passing through inverter 431. The negative of the voltage of the signal from envelope generator 432 slows the cycling rate of sequencer 440 in proportion to the incidence of the ongoing EEG signal exceeding the first threshold. A second threshold detector 441, such as a Moog 912 Schmidt trigger, derives a second control signal directly from the ongoing EEG signal. The second threshold is preferably set at a greater voltage level than first threshold detector 421. The second control signal resets the sequencer to the beginning of its sequence of notes. Thus, the sequencer slows whenever the ongoing EEG signal exceeds the first threshold and starts over whenever the ongoing EEG signal exceeds the second threshold.

Figure 5:
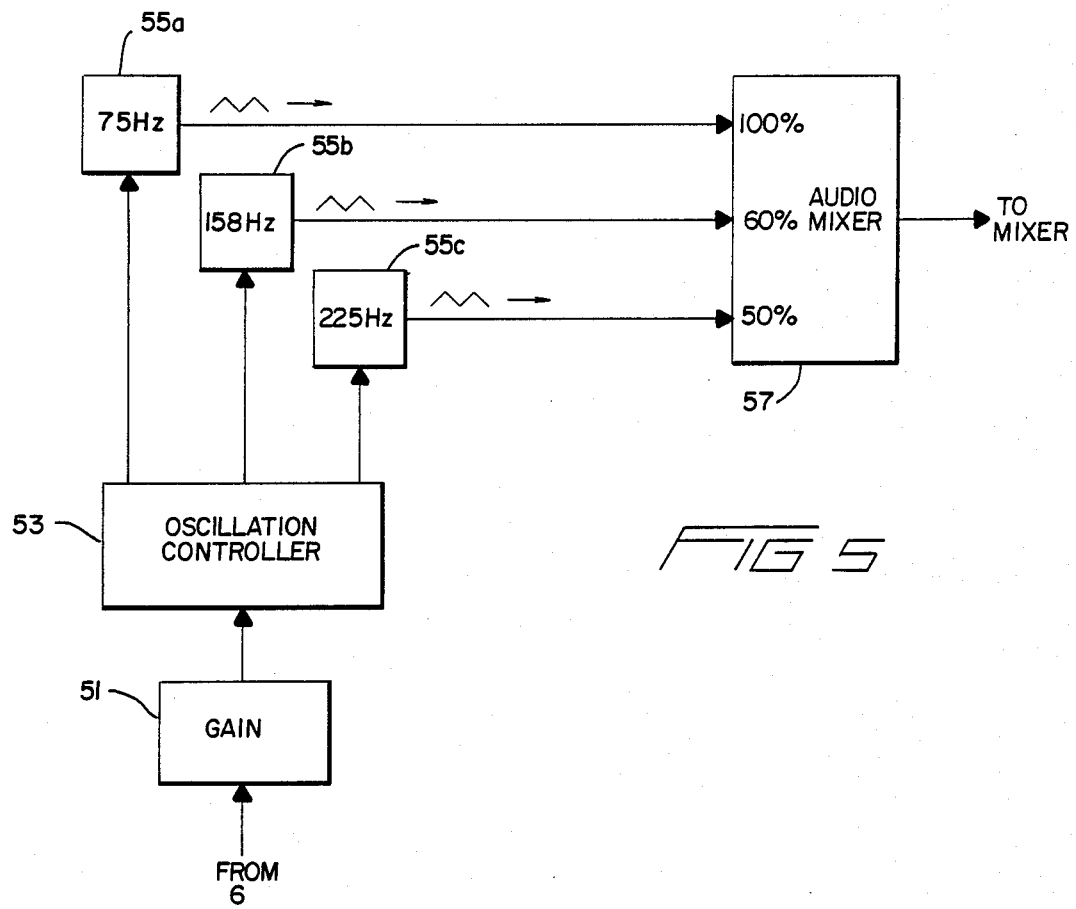
FIG. 5 is a block diagram of the frequency modulation unit shown in FIG. 4.

FIG. 5 is a more detailed functional block diagram of the frequency modulation unit 410 shown in FIG. 4. A Moog CP3A gain control unit 51 controls the amplitude of the ongoing EEG signal from line 6 that is supplied to a Moog 921A oscillation controller 53. The oscillator control 53 produces an output signal that controls the oscillation frequency of three Moog 921B voltage controlled oscillators, 55a, 55b and 55c, respectively, having base frequencies of 75 Hz, 158 Hz and 225 Hz, respectively. The output from the frequency oscillators comprise rich harmonic structures such as triangular wave forms. A Moog CP3A audio mixer 57 combines the output signals from the VCO's in the ratio of 10:6:5, respectively, as indicated by settings on the Moog mixer.

Figure 6:
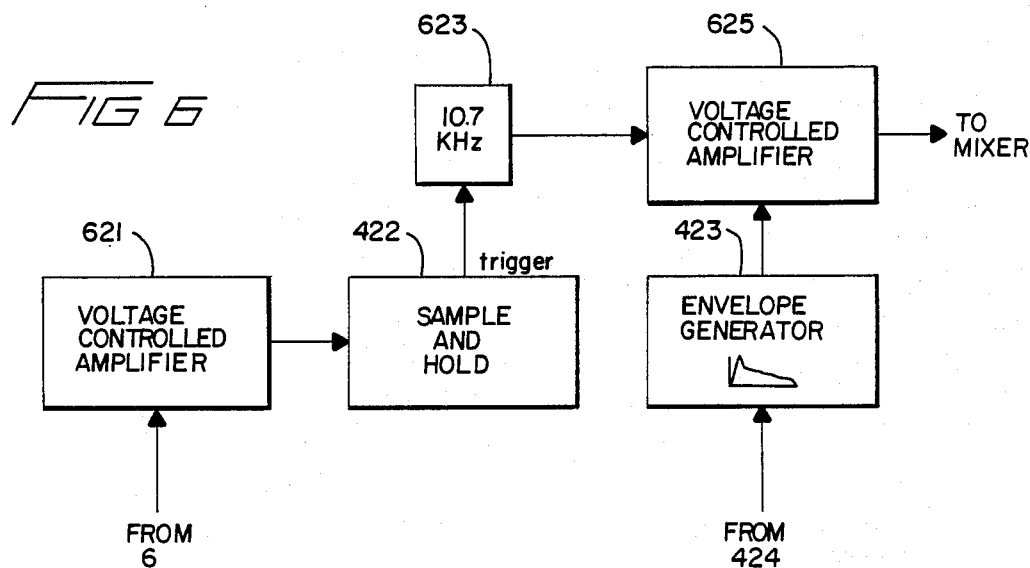
FIG. 6 is a block diagram of the bells unit shown in FIG. 4.

FIG. 6 shows a more detailed functional block diagram of the bells unit 420 and sample and hold unit 422 and envelope generator 423 shown in FIG. 4. A Moog 902 voltage controlled amplifier 621 directs the ongoing EEG signal from line 6 to a Moog 1528 sample and hold unit 422 from FIG. 4. The sample and hold unit is triggered by first threshold detector 421 to produce an output voltage that is proportional to the voltage of the ongoing EEG signal from signal bus 6. Once triggered, the sample and hold unit 422 determines the oscillation frequency of a Moog 921 voltage controlled oscillator 623 which has a center frequency of 10.7 KHz. A Moog 902 voltage controlled amplifier 625 receives an input signal from voltage oscillator 623 in the form of a triangular wave. A Moog 911 envelope generator 423 modulates the amplitude of the voltage output signal from VCA 625 so that the resulting audio output sounds like a bell and may therefore supply musical flavor to the resulting audio output. The envelope generator reaches maximum amplitude four milliseconds after being triggered by threshold detector 421. In order to bring the bell sound and FM sound into phase alignment, the FM sound should be delayed an additional 4 milliseconds, and this delay should be taken into account in calculating the delay time. The FM unit, however, is not shown as being so delayed. This relatively sharp rise time corresponds to a sharp attack time which is characteristic of a struck bell. The amplitude envelope then decays to 60% of maximum amplitude after 200 milliseconds. The generator shuts off after an additional 200 milliseconds so as to approximate the ringing of a bell.

Figure 7:
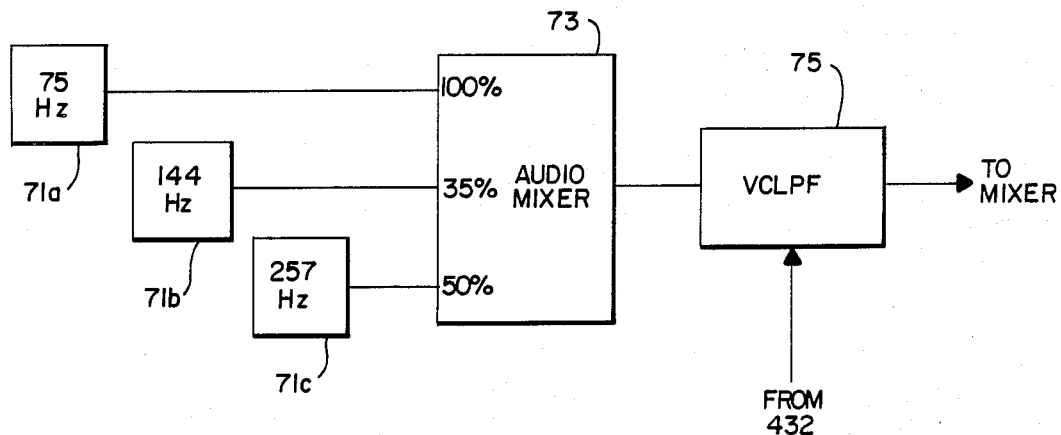
FIG. 7 is a block diagram of the overtone sweep unit shown in FIG. 4.

FIG. 7 is a more detailed functional block diagram of overtone sweep unit 430 shown in FIG. 4. A Moog CP3A audio mixer 73 mixes, in the ratio of 10:3.5:5, the triangular wave output signals from Moog 921 voltage controlled oscillators 71a, 71b and 71c, having base frequencies of of 75 Hz, 144 Hz, and 257 Hz, respectively. A Moog 904 A voltage controlled low pass filter 75 directs the output signal of audio mixer 73 to the main mixer after its timbre spectral content is modulated by envelope generator 432 of FIG. 4. Envelope generator 432 produces an output signal that reaches maximum value 500 milliseconds after being triggered by threshold detector 421. The amplitude of the output envelope then falls 70% of peak value over the next 400 milliseconds and completely shuts off after an additional 500 milliseconds. The total conduction time of envelope generator 432 is therefore greater than the expected duration of an alpha wave. Hence, a subsequent alpha wave increases or maintains at maximum the amplitude of the control signal and maintains or increases the amplitude of the overtone sweep. The envelope generator eventually shuts off at the end of an alpha burst.

Figure 8:
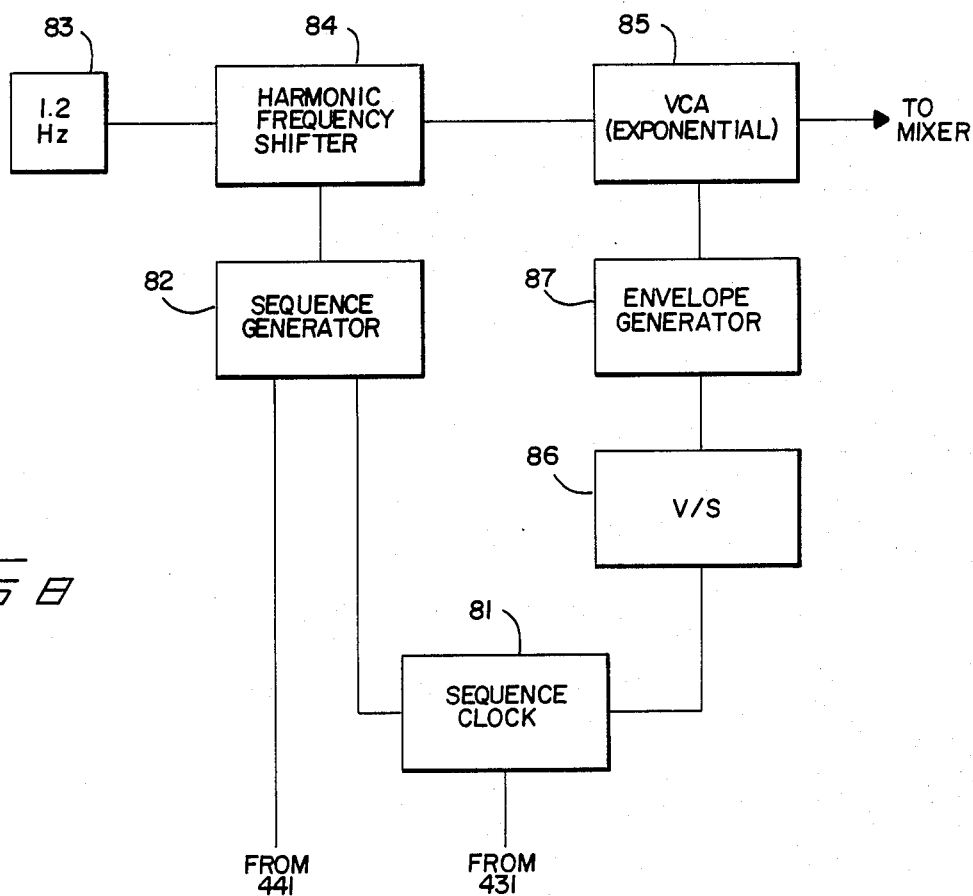
FIG. 8 is a block diagram of the sequencer unit shown in FIG. 4.

FIG. 8 is a more detailed block diagram of the sequencer unit 440 shown in FIG. 4. The output of envelope generator 432 is inverted by inverter 431, as shown in FIG. 4, to trigger a Moog 960 sequence clock controller 81 which supplies a clocking signal to sequence generator 82. The sequence generator has three rows of eight notes each for a total of 24 notes. The sequence generator cycles through the 24 notes at a fixed rate and modulates a Bode 1630 harmonic frequency shifter 84 which shifts the frequency of the square wave output signal from a Moog 901 B voltage controlled oscillator 83. The output signal from frequency shifter 84 passes through a Moog 902 voltage controlled amplifier 85 which is amplitude modulated by the output signal from a Moog 911 envelope generator 87 in response to a trigger signal from sequence clock controller 81.

The cycling rate of sequence generator 82 is reduced in proportion to the amplitude of a control signal from sequential controller 81 which is proportional to the voltage value of envelope generator control signal from first threshold detector 421. Sequence clock 81 also triggers envelope generator 87 through a Moog 961CP interface unit 86. The envelope generator adds musical flavor of the output signal from harmonic frequency shifter 84 by changing the output amplitude envelope to correspond to any desired instrument.

The sequential generator also comprises a control signal input for retriggering the sequence to the first row. Sequence generator 82 comprises a Moog 962 sequential switch which has three control ports for retriggering the sequential controller to any of the three columns. The output signal from threshold detector 441 uses a Moog 961CP interface to trigger the output switch to the first row and the sequence generator to the first column each time the ongoing EEG signal exceeds the second threshold level.

FIG. 9 is a flow chart of the signal processing steps such as performed by the apparatus disclosed in FIGS. 4-8. The ongoing EEG signal received at step 90 supplies a continuum of signal processing paths that ranges between following moment-by-moment change in the ongoing EEG signal to controlling independently generated sounds. Various intermediate signal processing paths respond to specific features or properties of the ongoing EEG signal in ways specifically engineered to incorporate multiple information pathways into the musical feedback signal. The music thus communicates a real time analysis of the ongoing EEG signal in a psychoacoustically correct form which can affect the biological activity of the brain when used in a real time resonance loop.

Referring to FIG. 9, the moment-by-moment change in the ongoing EEG signal is communicated at step 91. The preferred method for indicating moment-by-moment change is to frequency modulate a tone chord with ongoing EEG signal. Frequency modulation is preferred because the human auditory system is more than 30 times more sensitive to changes in frequency. The output signal from step 91 supplies an input signal to mixing step 92. This first level of signal processing provides the most immediate possible indication of current EEG activity.

Another level of EEG signal processing and analysis extracts major features of the EEG and reinforces them by sounding whenever the EEG signal generates the predetermined feature sensed at conditional test 94. No output is generated in the absence of the feature of interest. Any of several sounds might be generated to reinforce the particular features. However, no sound is absolutely physiologically correct if its attack time peak intensity exceeds the duration of the EEG feature that is being reinforced because a sound having a longer duration permits preceding features to obscure subsequent occurrences of the same feature. For example, reinforcing each peak for alpha activity having a frequency of approximately 10 Hz requires a sound having an attack time of less than 100 milliseconds. A bell, chime or harp sound is preferred because it has a sufficiently short attack time and is also psychologically musically pleasing to the listener and thus adds musical flavor to the feedback music.

Another level of signal analysis and processing of the ongoing EEG signal comprises generating an indication of the current flavor of the ongoing EEG signal. The current flavor may be indicated by generating an overtone sweep at step 97 in response to a feature such as a crest of the ongoing EEG signal. The ongoing EEG thus changes the musical flavor of the feedback music by increasing the harmonic content of the feedback as the ongoing EEG signal first exhibits the preferred activity and then continues to pass more harmonics with repeated instances of the preferred activity. The overtone sweep provides a more derivative indication of ongoing physiological activity since its production is not engineered to evoke an immediate response. Nevertheless, the overtone sweep is a relevant indication of ongoing EEG activity and the extent of the production of a particular type of EEG activity.

Yet another level of signal analysis and processing of the ongoing EEG signal comprises generating an indication of the time average of the musical flavor in a manner that is analogous to conventional biofeedback. The time average flavor can be indicated by modifying a sequence of notes at step 98 in response to some property of the ongoing EEG signal such as its relative amplitude. Further, the sequence of notes can supply considerable musical flavor to the acoustical output independent of the ongoing EEG signal to make the feedback music psychologically pleasing for extended periods of time.

As shown in FIG. 9, the feature extraction, current flavor and average flavor signal processing levels all respond to a common feature of the ongoing EEG signal detected at conditional step 94. The multiple information pathways thus tend to reinforce the same physiological activity in different ways even while being derivative of moment-by-moment changes in the ongoing EEG signal. In addition, additional musical flavor may be triggered in response to other characteristics of the ongoing EEG signal as indicated by conditional test 99. It is to be appreciated that the musical flavor provides both current physiological information and more perceptually discernible time average learning information that enables a person to learn to control his EEG activity.

It has been found that particular utility can be obtained by organizing the information pathways in musical form. For example, the current musical flavor and feature extraction sounds, and long term flavor sound can be made to function as counter melodies of one another to add musical texture to the feedback. The relative perceptual prominence of each voice can be made to change so as to indicate the relative magnitude of a desired brain state as described in the summary of the invention section.

It is to be appreciated that the signal processing steps performed in the flow chart shown in FIG. 9 may be implemented with different apparatus, including preferably apparatus using the techniques of digital sound synthesis, to produce an apparatus that operates in accord with the teachings of the present invention. Numerous additional musical voices may be added to the output. Other musical relationships can be established between the musical voices, either permanently or through time-variant means.

ALTERNATE EMBODIMENTS

A modification to the embodiment of the invention shown in FIG. 1 involves measuring the ongoing EEG signal from additional locations on the scalp and modifying the acoustical feedback to simultaneously enhance the EEG at several locations, or to enhance it at one location while discouraging its production at another location. For example, it is thought to be preferable for reinforcing alpha wave activity with an electrode at the P3 location to direct physiological information, i.e. the frequency modulated tone chord and bell sound to the right ear and the overtone sweep and note sequence to the left ear. In terms of dichotic listening, the physiological stimulation thus is confined to the left side of the brain because sound heard with the right ear stimulates the left side of the brain. The right side of the brain is thus free to produce other types of EEG activity such as beta waves. The literature suggests that alpha activity at P3 with corresponding beta activity in the temporal lobe of right brain corresponds to a state of inwardly focused attention with positive emotional imagery. Further, right brain is better able to holistically process the learning information communicated by the note sequencer and overtone sweep, and respond to its changing musical structure.

It is to be appreciated that the signal processing steps shown in FIGS. 2 and 4 may be implemented with digital musical equipment. Indeed, digital sound synthesis techniques are thought to be preferable because a wide range of voices may be implemented in response to a wider range of phenomena present in the ongoing EEG signal. The particular EEG phenomena used to produce a voice and the musical structure of the voice may be selected, on an experimental basis, to produce a desired physiological response. Further, digital equipment permits more precise feature extraction as well as automatic scaling of the triggering thresholds during use so that the feedback music continues to induce the appropriate response in the person as his EEG parameters change throughout the session and he enters deeper into the desired state. Alternately or additionally, the musical voices may be organized by a composer based on purely aesthetic considerations. Digital analysis and synthesizing equipment greatly simplifies composing and implementing of the acoustical feedback by reducing the amount and time consumed in experimentally finding physiologically and psychoacoustically "correct" sounds.

Additional voices may be added to create interesting and physiologically relevant effects. Both the type of musical sound produced and the quality of that sound directly affect the ability of the present invention to enhance brain wave activity. The criteria used to select a proper sound have been described above. The musical quality of the feedback music must exceed an as of yet indefinite minimum threshold to allow the resonance feedback effect to proceed.

One unusual result obtained with the present invention is the production of synesthesic effects, or the observations of lights and colors, in response to the various musical voices in the resonance feedback. Specific colors or color patterns have been observed to follow particular voices in the music. Synesthesic effects have been experienced by approximately one third of individuals tested using the principles of the present invention. This result suggests that the addition of visual feedback may augment the effects obtained with acoustical feedback.

APPLICATIONS

The present invention is useful for producing enjoyable music. For example, the second voice can comprise a bell sound, chime or any other desired tone. Likewise, the sequencer may play twenty-four notes from any desired type of instrument to produce any type of melody. The invention may be used as a musical instrument on which a person may learn and play music by cognitive control without also having to physically perform a composition.

The invention may be used as a relaxation device that operates by resonantly reinforcing high amplitude, low frequency EEG activity such as alpha wave activity. Such biofeedback also permits an individual to monitor and change his brain wave patterns to obtain various internal states. A clinical psychologist may facilitate various therapeutic procedures, such as guided imagery, by enhancing or retarding a particular brain state. A neurologist may use the present invention as a musically pleasing test of brain functions by introducing a controlled signal, such as punctate sounds embedded within the feedback music, to generate an evoked potential response. Yet another application is as a clinical monitoring device which permits a physician or researcher, such as an anesthesiologist, to monitor the status of a patient's or subject's brain over a loudspeaker without having to maintain a constant vigil on the visual image formed on an oscilloscope.

Experiments have shown that the present invention provides an individual with a pleasant way to control his brain wave activity within a matter of a few minutes. Moreover, individuals who have experienced biofeedback resonance according to the present invention have shown a statistically significant reduction in anxiety. The present invention appears to actively promote alpha wave activity since the amount of alpha activity increases during feedback in contradistinction to no sound or a noncontingent, but in other respects similar, acoustical stimulus. In contrast, nonresonance biofeedback techniques may block alpha wave activity with an incongruent feedback signal.

The invention can be used to diagnose psychological and neurological conditions. The dramatic portrayal of the emotional and functional states of an individual contained in the feedback music provides a direct indication of the psychological state of a person. Empirical guidelines should be established to enable a practitioner to critically and analytically listen to the feedback music and form diagnostic opinions about the individual. Further, the invention could be used to create diagnostic methods for assessing hearing disorders after traumas such as stroke or head injury because the source of the EEG signal used to create the feedback music and the efficacy of the feedback can be precisely defined. The invention may also be useful for mapping brain activity in relation to the production or perception of music or language.

An additional application of the present invention is to the general field of man/machine interface such as between the human brain and a computer. Experiments have shown that the present invention enables individuals to control their EEG activity so as to repeat audible patterns. The human brain can easily remember and distinguish between a large number of musical patterns such as melodies. Individuals should be able to remember and reliably reproduce a large number of distinct control signals. Thus, referring to FIG. 1, speaker 13 may be replaced by a pattern recognition device which, after recognizing a desired musical pattern, generates the appropriate control signal to a device which is not necessarily a musical device.

The present invention also permits interpersonal communications. One skilled in the art may readily appreciate that various voices may be added to the feedback signal that indicate a particular synchronism or mental state among more than one individual. The musical feedback thus comprises a form of communication which is analogous to the type of communication which occurs between, for example, a violin and a cello playing a duet. In the present instance, however, the communication comprises a form of cognitive "group thought" and emotional communication not hitherto known.

EXAMPLE 1

Figure 10:
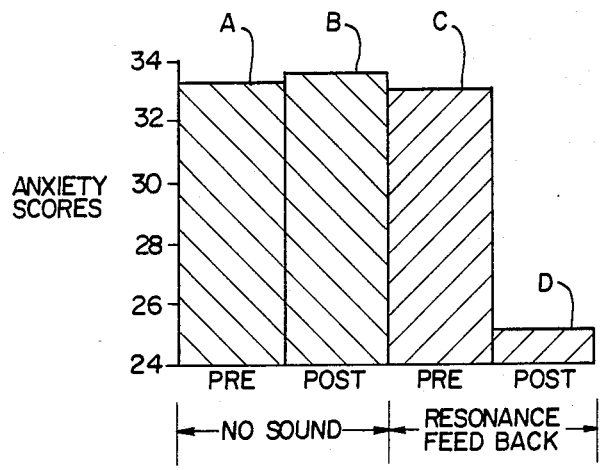
FIG. 10 illustrates the ability of the present invention to induce relaxation in human beings.

The capabilities of the present invention to induce relaxation are illustrated by the experimental results presented in FIG. 10. A sample group of 15 subjects was selected. No subject was a clinical patient and none exhibited signs of psychopathology. Each subject experienced a ten minute control period of sitting quietly without sound, followed by a ten minute period of resonance feedback. The state of anxiety of each subject was measured before and after the ten minute periods using the Spielberger self report anxiety scale. The Spielberger scale is well known to those skilled in the art. The ordinate of FIG. 10 shows the relative anxiety scores as measured by the Spielberger scale. Scores in the range of 45 to 50 correspond to overt signs of anxiety. Scores in the mid 30's indicate moderately high levels of anxiety. The lowest possible score on the scale is 20.

As shown in FIG. 10, quiet did not significantly change the level the anxiety as seen by comparing the scores for blocks A and B obtained before and after the period of quiet, respectively. Measurements remained in the mid-30's. After resonance feedback, however, anxiety decreased markedly from the mid-30's to the mid-20's as shown by comparing blocks C and D corresponding to scores obtained before and after resonance feedback, respectively. The decrease in anxiety as a result of resonance feedback was significant at the $P<0.05$ level of statistical significance.

EXAMPLE 2

Figure 11:
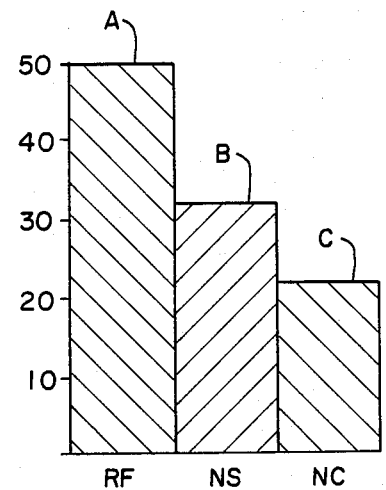
FIG. 11 illustrates the ability of the musical feedback of the present invention to induce increased alpha activity using a physiological resonance feedback loop.

FIG. 11 exemplifies the increase in alpha activity in a single subject during resonance feedback. The ordinate corresponds to the number of alpha waves counted during a 30 second period at the CZ location on the scalp. FB corresponds to the wave count obtained from a single representative individual experiencing resonance feedback, In contrast, NS represents the alpha count for a control condition corresponding to a comparable period without sound. NC corresponds to the alpha count for the same individual listening to the music corresponding to his own brain wave activity but which has been delayed by a few minutes so as not to be contingent on the ongoing EEG signal. FIG. 11 clearly illustrates that the resonance feedback produces a greater number of alpha waves than obtained by mere silence. Further, the greater number of alpha waves obtained with resonance feedback as opposed to music that is not contingent upon the ongoing EEG signal shows the importance of resonance feedback at inducing the desired form of EEG activity.

EXAMPLE 3

Figure 12:
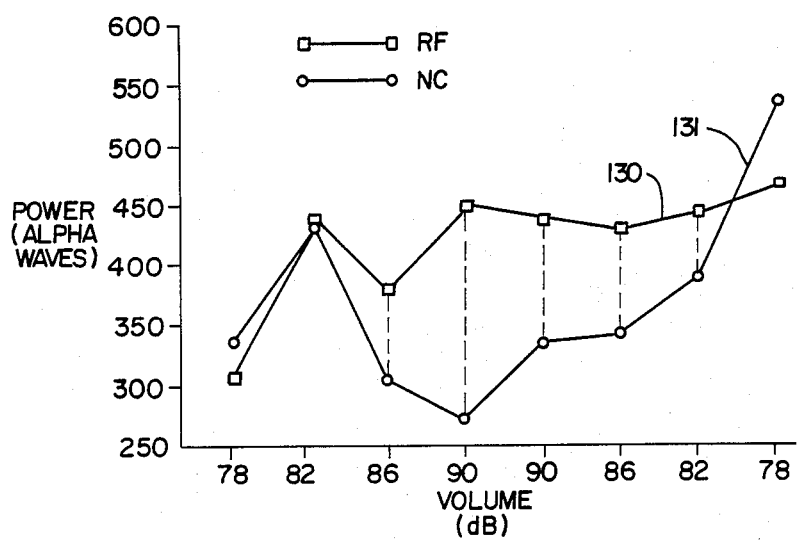
FIG. 12 illustrates the threshold at which alpha activity is induced by increasing the intensity of the acoustical feedback signal in resonance mode compared with the same type of music played so as not to be contingent on ongoing EEG activity.

FIG. 12 corresponds to a representative comparison of the effects of resonance feedback at various decibel intensity levels for a single subject for a single subject. The vertical scale corresponds to the relative power present in the alpha wave signal as measured by an electrode attached to the CZ location on the scalp (400 units=13.6 microvolts). The horizontal axis corresponds to the intensity of the feedback in decibels. Referring to FIG. 12, it is apparent that the amount of alpha activity present with resonance feedback, represented by curve 130, diverges substantially at approximately 86 decibels from that produced with the same type of music played as noncontingent sound as represented by curve 131. Further, the amount of alpha activity measured with resonance feedback and noncontingent feedback begins to converge as the intensity declines at approximately 82 decibels. It is to be appreciated that an intensity of 86 decibels corresponds to approximately the volume produced by a home stereo system operating at moderately high listening levels. Further, the amount of alpha activity generated with resonance feedback appears to increase with intensity after 86 decibels. In contrast, the amount of alpha wave activity produced by the noncontingent feedback decreases with increasing intensity as illustrated by the minimum in curve 131 at maximum intensity. Experiments conducted with several individuals have shown that the 86 decibel threshold, in the context of current signal to noise ratios, appears to be critical to the commencement of resonance feedback.

EXAMPLE 4

Figure 13A:
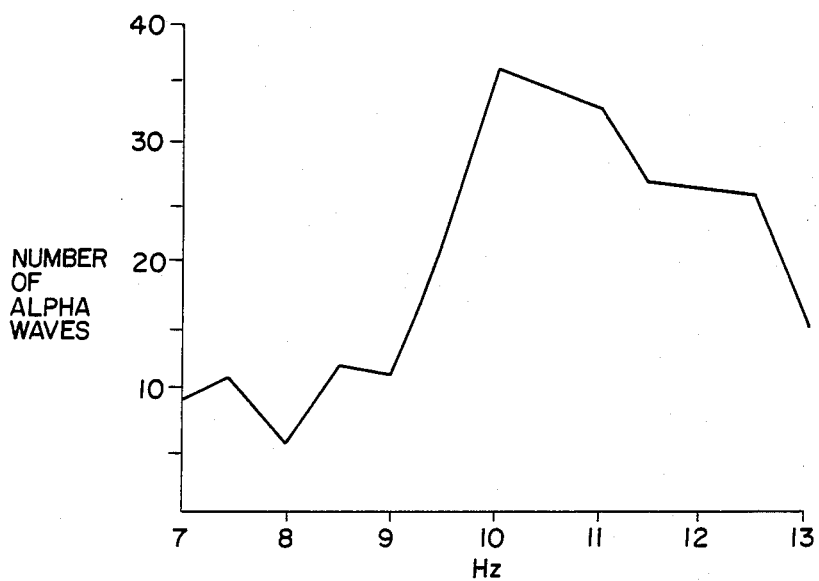
FIGS. 13 and 14 illustrate how the amount of alpha wave activity can be maximized by adjusting the delay time used in the resonance feedback loop to coincide with the frequency of the brain wave activity that the brain is predisposed to produce.
Figure 13B:
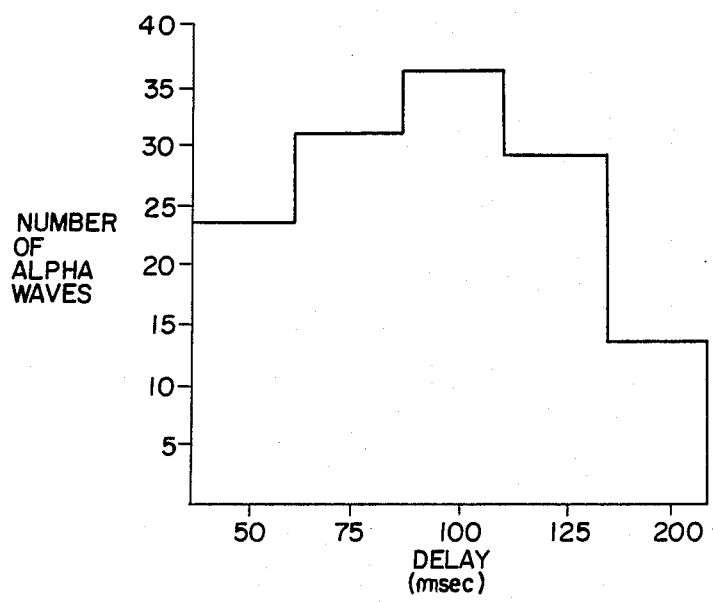

FIGS. 13 and 14 illustrate the importance of the delay period to maximize resonance feedback. FIG. 13a shows the distribution of alpha waves with frequency at the P3 location on the scalp of a representative individual. The ordinate corresponds to the number of EEG waves observed during a 30 second interval and the horizontal axis shows the range in frequencies obtained by using a cross point analysis. This particular individual exhibits maximum alpha Wave activity at 10 Hz. In FIG. 13b, the vertical axis represents the alpha wave count and the horizontal axis represents the total delay time in milliseconds obtained during resonance feedback using the present invention. The optimal amount of alpha wave activity was obtained with a delay time of 100 milliseconds which corresponds to a frequency of 10 Hz having a period of 100 milliseconds. Thus, the optimal delay time exactly corresponds to the preferred alpha frequency of this subject.

Figure 14A:
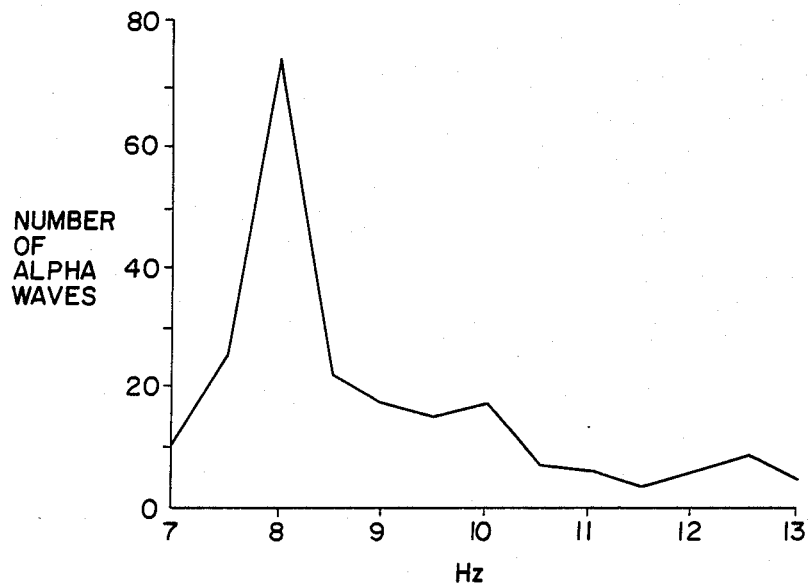
Figure 14B:
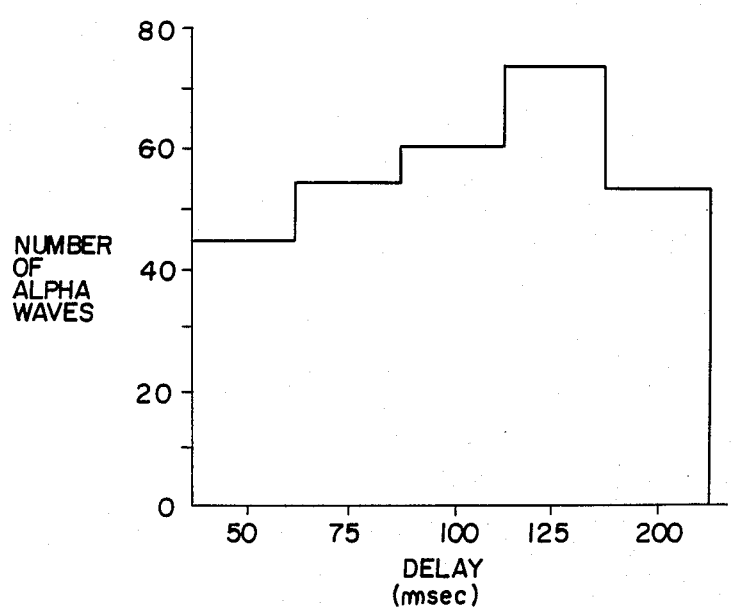

FIG. 14 shows similar results for a second representative individual. As shown in FIG. 14a, this individual has a preferred alpha frequency of 8 Hz which corresponds to a period of 125 milliseconds. FIG. 14b shows that the maximum amount of alpha wave activity obtained using the the present invention occurred with a total delay time of 125 milliseconds which, again, corresponds to the preferred EEG alpha frequency. Thus, for any particular individual the preferred frequency of the desired EEG activity determines the optimal delay time present in the resonance feedback loop. Resonance is maximized by matching the feedback time delay to the frequency at which the brain prefers to produce the EEG activity of interest.

SUGGESTIONS FOR FURTHER RESEARCH

Numerous possible applications of the present invention have been described above. A particularly promising application is the use of resonance feedback as an an alternative to conventional invasive brain stimulation techniques.

Current methods of brain stimulation involve surgically implanting an electrode into an region of the brain that is to be stimulated. The resulting effect on the brain depends on the location of the electrode and the frequency of the stimulation. For example, a region of the brain can be activated with high frequency stimulation, whereas inhibition and deactivation result from low frequency stimulation. The process of surgically implanting an electrode, however, is highly invasive and greatly limits the both research into brain stimulation and its utility as a diagnostic or therapeutic tool.

In contrast, resonance feedback uses noninvasive electrodes that are located on the scalp. The position of the electrodes determines the area of the brain that is "stimulated" by the feedback music. Further, the use of constructive and destructive interference, selective filtering and judicious manipulation of delay times may produce different frequencies of "stimulation". Resonance feedback thus offers the possibility of systematically stimulating selected areas of the brain.

One potential application for brain stimulation using resonance feedback involves neural exercise. Rehabilitation programs for persons who have suffered brain injuries are essentially designed around the concept of neural exercise, wherein the region of the brain that surrounds a region that has been damaged is systematically stimulated in the hope that it will assume the functions of the damaged brain cells. It is thought likely that resonance feedback is effective at stimulating neural activity in a selected region of the brain and should therefore serve as a form of neural exercise. Resonance feedback is thought to offer particular utility in cases involving music and language impairment.

Recent developments in superconductivity and research directed to recording brain waves with magnometers indicate that increased resolution and selectivity may soon be available to aid resonance stimulation of any region of the brain. Magnometers may replace the scalp electrode 3 shown in FIG. 1 to generate an input signal corresponding to the semiperiodic changes in amplitude of the magnetic field that are associated with ongoing EEG activity. Magnometers can triangulate the semiperiodic magnetic activity so as to generate a signal indicative of EEG activity occurring in a well defined region deep within the brain. The delay inserted into the feedback loop can be adjusted to obtain a desired phase relationship between the feedback signal and the ongoing EEG activity since magnometers can also be used to determine the response of the region of the brain to acoustic stimulation.

In addition, EEG computer analysis methods, such as BEAM developed by Frank Duffy, are providing extensive maps of the brain that indicate what EEG activity in which regions of the brain are associated with particular states of emotion, cognition and consciousness. This information can be used as a guide for designing resonance feedback protocols and in selecting regions of the brain for resonance stimulation.

The principles, preferred embodiments and modes of operation of the present invention have been described in the foregoing specification. The invention, which is intended to be protected herein, should not, however, be construed as limited to the particular forms described, or the particular examples given, as these are to be regarded as illustrative rather than restrictive. Variations and changes may be made by those skilled in the art without departing from the spirit of the invention. Accordingly, the foregoing detailed description should be considered exemplary in nature and as in no way limiting to the scope and pioneering spirit of the invention as set forth in the appended claims.

What is claimed is:

1. A biofeedback apparatus useful for creating music, comprising:
   means for receiving an ongoing EEG signal from at least one region of the brain of a biological entity, said at least one region of the brain responding to acoustical stimulation, said ongoing EEG signal having a voltage amplitude exhibiting semiperiodic change;
   means for translating said ongoing EEG signal into music, said translating means including
      means for generating an acoustical indication of the semiperiodic change in said ongoing EEG signal, and
      means for generating musical flavor and adding said musical flavor to said acoustical indication;
   means for directing said music so as to be received by the brain; and
   means for delaying said directing means for a period of time determined so that the brain response to said music occurs with a predetermined phase relationship with respect to the ongoing EEG signal received from said region of the brain.

2. A biofeedback apparatus as claimed in claim 1, further comprising means for anticipating an occurrence of said semiperiodic change in said ongoing EEG signal.

3. A biofeedback apparatus as claimed in claim 2, wherein said anticipating means comprises means for determining a preferred frequency at which said brain produces said semiperiodic change over a predetermined period of time.

4. A biofeedback apparatus as claimed in claim 2, wherein said anticipating means comprises means for determining a period for a most recent preceding semiperiodic change.

5. A biofeedback apparatus as claimed in claim 2, further comprising means for modifying said delaying means to correspond to said anticipated occurrence of said semiperiodic change in said ongoing EEG signal.

6. A biofeedback apparatus as claimed in claim 2, wherein said means for generating said acoustical indication comprises means for generating sound selected from the group consisting of:
   a tone chord that is frequency modulated with said ongoing EEG signal;
   a punctate sound having a short attack time that is produced in response to a predetermined recurrent feature of said ongoing EEG signal; and
   timbre modulation produced by modulating an overtone sweep with said ongoing EEG signal.

7. A biofeedback apparatus as claimed in claim 6, wherein the generated sound is a punctate sound and said means for generating said punctate sound comprises means for generating a sound selected from the group consisting of:
   a bell;
   a drum; and
   a harp.

8. A biofeedback apparatus as claimed in claim 6, wherein the generated sound is a punctate sound and said means for generating said punctate sound comprises means for generating a bell sound in response to a local maxima in said ongoing EEG signal.

9. A biofeedback apparatus as claimed in claim 2, wherein:
   said means for generating said acoustical indication comprises means for generating a tone chord; and
   means for frequency modulating said tone chord with said ongoing EEG signal.

10. A biofeedback apparatus as claimed in claim 9, wherein said means for generating musical flavor further comprises means for modulating an overtone sweep with a low frequency, pseudorandom control signal.

11. A biofeedback apparatus as claimed in claim 9, wherein said means for generating musical flavor comprises:
   means for generating a timbre modulated tone chord that is modulated with a low frequency, pseudorandom control signal; and
   means for generating a timbre modulated chord that is modulated with the voltage amplitude of said ongoing EEG signal.

12. A biofeedback apparatus as claimed in claim 9, wherein said means for generating musical flavor comprises means for generating a sound selected from the group consisting of:
   a timbre modulated tone chord that is modulated with a low frequency, pseudorandom control signal;
   a punctate sound having a short attack time that is produced in response to a predetermined recurrent feature of said ongoing EEG signal;
   a timbre modulated tone chord that is modulated with said ongoing EEG signal; and
   a sequence of musical notes.

13. A biofeedback apparatus as claimed in claim 12, wherein the generated sound is a punctate sound and said means for generating said punctate sound further comprises means for generating a sound selected from the group consisting of:
   a bell;
   a drum; and
   a harp.

14. A biofeedback apparatus as claimed in claim 12, wherein the generated sound is a punctate sound and said means for generating said punctate sound comprises means for generating a bell sound in response to a local maxima in said ongoing EEG signal.

15. A biofeedback apparatus as claimed in claim 12, wherein the generated sound is a sequence of musical notes; and
   said means for generating said sequence of notes comprises means for generating said notes at a predetermined rate; and
   means for slowing said rate in proportion to the frequency of occurrence of high amplitude waves of said ongoing EEG signal.

16. A biofeedback apparatus as claimed in claim 15, further comprising means for triggering said slowing means only when the amplitude of said ongoing EEG signal exceeds a first predetermined threshold level.

17. A biofeedback apparatus as claimed in claim 16, further comprising means for generating said sequence of notes over again when the amplitude of said ongoing EEG signal exceeds a second predetermined threshold level that is greater than said first predetermined threshold level.

18. A biofeedback apparatus as claimed in claim 15, further comprising means for generating said sequence of notes over again when the amplitude of said ongoing EEG signal exceeds a second predetermined threshold level that is greater than said first predetermined threshold level.

19. A biofeedback apparatus as claimed in claim 9, wherein said means for generating an acoustical indication of the semiperiodic change in said ongoing EEG signal produces a first musical voice.

20. A biofeedback apparatus as claimed in claim 19, wherein said musical flavor comprises:
   means for generating a second musical voice indicative of a predetermined feature of said ongoing EEG signal;
   means for generating a third musical voice indicative of the occurrence of a semiperiodic predetermined feature of the ongoing EEG signal; and
   means for generating a fourth musical voice indicative of an average value of the ongoing EEG signal.

21. A biofeedback apparatus as claimed in claim 20, wherein:
   said means for generating said first musical voice comprises means for generating a tone chord and means for frequency modulating said tone chord with said ongoing EEG signal;
   said means for generating said second musical voice comprises means for generating a bell sound in response to a local maxima of said ongoing EEG signal;
   said means for generating said third musical voice comprises means for generating an overtone sweep of a chord tone, said overtone sweep being modulated by the amplitude of said ongoing EEG signal at a local maxima; and
   said means for generating said fourth musical voice comprises means for generating a series of notes in sequence at a rate determined by the amplitude of said ongoing EEG signal.

22. A biofeedback apparatus as claimed in claim 21, wherein:

said means for generating said second voice comprises means for not generating said second voice unless the amplitude of said ongoing EEG signal exceeds a first predetermined threshold level; and said means for generating said fourth voice comprises means for not generating said sequence rate at a slower rate unless the amplitude of said ongoing EEG signal exceeds said first threshold level.

23. A biofeedback apparatus as claimed in claim 22, wherein:
said means for generating said third voice comprises means for not generating said third voice unless the amplitude of said ongoing EEG signal exceeds said first threshold level; and
said means for generating said sequence of notes comprises means for generating said sequence again whenever said ongoing EEG signal exceeds a second predetermined threshold level that is greater than said first predetermined threshold level.

24. A biofeedback apparatus as claimed in claim 23, wherein said means for generating said sequence of notes comprises means for generating a progressively more dissonant pattern.

25. A biofeedback apparatus as claimed in claim 23, wherein said means for generating said second voice comprises means for modulating the pitch of said bell sound around a center frequency in proportion to said amplitude of said ongoing EEG signal.

26. A biofeedback apparatus as claimed in claim 23, wherein said means for generating said fourth voice comprises an envelope generator means for amplitude modulating said fourth voice, said envelope generator means being triggered independently of said ongoing EEG signal.

27. A method of producing a biofeedback signal useful for creating music, comprising the steps of:
receiving an ongoing EEG signal from at least one region of the brain of a biological entity, said at least one region of the brain responding to acoustical stimulation, said ongoing EEG signal having a voltage amplitude exhibiting semiperiodic change;
translating said ongoing EEG signal into music, including the steps of
generating an acoustical indication of the semiperiodic change in said ongoing EEG signal,
generating a musical flavor, and adding said musical flavor to said acoustical indication;
directing said music so as to be received by the brain; and
delaying said directing for a period of time determined so that the brain responds to said music with a predetermined phase relationship with respect to the ongoing EEG signal received from said region of the brain.

28. A method of producing a biofeedback signal as claimed in claim 27, further comprising the step of anticipating an occurrence of said semiperiodic change in said ongoing EEG signal.

29. A method of producing a biofeedback signal as claimed in claim 28, wherein said step of anticipating comprises the step of determining a preferred frequency at which said brain produces said semiperiodic change over a predetermined period of time.

30. A method of producing a biofeedback signal as claimed in claim 28, wherein said step of anticipating comprises the step of determining a period for a most recent preceding semiperiodic change.

31. A method of producing a biofeedback signal as claimed in claim 28, further comprising the step of modifying said delaying time period to correspond to anticipated occurrence of said semiperiodic change in said ongoing EEG signal.

32. A method of producing a biofeedback signal as claimed in claim 28, wherein said step of generating said acoustical indication comprises the step of generating a sound selected from the group consisting of:
a tone chord that is frequency modulated with said ongoing EEG signal;
a punctate sound having a short attack time that is produced in response to a predetermined recurrent feature of said ongoing EEG signal; and
timbre modulation produced by modulating an overtone sweep with said ongoing EEG signal.

33. A method of producing a biofeedback signal as claimed in claim 32, wherein the generated sound is punctate and said step of generating said punctate sound comprises generating a sound selected from the group consisting of:
a bell;
a drum and
a harp.

34. A method of producing biofeedback as claimed in claim 33 wherein said step of adding musical flavor to said acoustical indication comprises the step of modifying said musical flavor with said ongoing EEG signal.

35. A method of producing biofeedback as claimed in claim 34, wherein:
said step of generating said acoustical indication comprises generating a tone chord and the step of frequency modulating said tone chord with said ongoing EEG signal; and
said step of adding musical flavor comprises the step of timbre modulating said tone chord with the voltage amplitude of said ongoing EEG signal.

36. A method of producing biofeedback as claimed in claim 35, wherein said step of adding musical flavor further comprises the step of modulating said timbre of said tone chord with an independently produced signal that is independent of said ongoing EEG signal.

37. A method of producing biofeedback as claimed in claim 36, wherein said independently produced signal comprises a low frequency, pseudorandom signal.

38. A method of producing biofeedback as claimed in claim 34, wherein said step of generating said acoustical indication of the semiperiodic change in said ongoing EEG signal produces a first musical voice.

39. A method of producing biofeedback as claimed in claim 38, wherein said step of generating musical flavor comprises the steps of:
generating a second musical voice indicative of a predetermined feature of said ongoing EEG signal;
generating a third musical voice indicative of the recent amplitude of the ongoing EEG signal; and
generating a fourth musical voice indicative of an average value of the ongoing EEG signal.

40. A method of producing biofeedback as claimed in claim 39 wherein:
said step of generating said first musical voice comprises the step of generating a tone chord that is frequency modulated with said ongoing EEG signal;
said step of generating a second musical voice comprises the step of generating a bell sound in response to a local maxima of said ongoing EEG signal;

said step of generating said third musical voice comprises the step of generating an overtone sweep of a chord tone, said overtone sweep being modulated by the relative frequency of occurrence of an at least semiperiodic predetermined feature of said ongoing EEG signal; and said step of generating said fourth musical voice comprises the step of generating a series of notes that are played in sequence at a rate determined by the amplitude of said ongoing EEG signal.

41. A method of producing biofeedback as claimed in claim 40, wherein:

said step of generating said second voice is performed only in response to the amplitude of said ongoing EEG signal exceeding a first predetermined threshold level; and said step of generating said fourth voice comprises the step of slowing said sequence rate in proportion to the amplitude of said ongoing EEG signal only when said ongoing EEG signal exceeds said first threshold level.

42. A method of producing biofeedback as claimed in claim 41, wherein:

said step of generating said third voice comprises the step of modifying said third voice only when the amplitude of said ongoing EEG signal exceeds said first predetermined threshold level; and said step of generating said fourth voice comprises the step of generating said sequence again whenever said ongoing EEG signal exceeds a second threshold level that is greater than said first threshold level.

43. A method of producing biofeedback as claimed in claim 42, wherein said sequence of notes comprises a progressively more dissonant pattern.

44. A method of producing biofeedback as claimed in claim 42, wherein said step of generating said second voice comprises the step of modulating the pitch of said bell sound around a center frequency in proportion to said amplitude of said ongoing EEG signal.

45. A method of producing biofeedback as claimed in claim 42, wherein said step of generating said fourth voice comprises the step of modifying the biofeedback signal with a signal that is independent of said ongoing EEG signal.

46. Music as derived by the process claimed in claim 39, wherein said steps of generating said acoustical indication and said musical flavor comprise generating a polyphonic hierarchy of musical voices that are mutually physiologically and psychoacoustically correct.

47. Music as derived by the process claimed in claim 46, wherein said first, second, third and fourth musical voices comprise sounds selected from the group consisting of:

a timbre modulated tone chord that is modulated with the ongoing EEG signal;

a punctate sound having a short attack time that is short relative to and produced in response to a predetermined recurrent feature of said ongoing EEG signal;

a timbre modulated tone chord that is modulated with said ongoing EEG signal; and a sequence of dissonant musical notes.

48. A method of producing a biofeedback signal as claimed in claim 32, wherein the generated sound is punctate and said step of generating said punctate sound comprises the step of generating a bell sound in response to a local maxima in said ongoing EEG signal.

49. A method of producing a biofeedback signal as claimed in claim 28, wherein:

said step of generating said acoustical indication comprises the step of generating a tone chord and the step of frequency modulating said tone chord with said ongoing EEG signal.

50. A method of producing a biofeedback signal as claimed in claim 49, wherein said step of generating musical flavor further comprises the step of modulating an overtone sweep with a low frequency, pseudorandom control signal.

51. A method of producing a biofeedback signal as claimed in claim 49, wherein said step of generating musical flavor comprises the steps of:

generating a timbre modulated tone chord that is modulated with a low frequency, pseudorandom control signal; and generating a timbre modulated chord that is modulated with the voltage amplitude of said ongoing EEG signal.

52. A method of producing a biofeedback signal as claimed in claim 49, wherein said step of generating musical flavor comprises the step of generating a sound selected from the group consisting of:

a timbre modulated tone chord that is modulated with a low frequency, pseudorandom control signal;

a punctate sound having a short attack time that is produced in response to a predetermined recurrent feature of said ongoing EEG signal;

a timbre modulated tone chord that is modulated with said ongoing EEG signal; and a sequence of musical notes.

53. A method of producing a biofeedback signal as claimed in claim 52, wherein the generated sound is punctate and said step of generating said punctate sound further comprises the step of generating a sound selected from the group consisting of:

a bell;

a drum and a harp.

54. A method of producing a biofeedback signal as claimed in claim 52, wherein the generated sound is a punctate sound and said step of generating said punctate sound further comprises the step of generating a bell sound in response to a local maxima in said ongoing EEG signal.

55. A method of producing a biofeedback signal as claimed in claim 52, wherein the sound is a sequence of musical notes, and said step of generating said sequence of notes comprises the step of generating said notes at a predetermined rate; and the step of slowing said rate in proportion to the frequency of occurrence of high amplitude waves of said ongoing EEG signal.

56. A method of producing a biofeedback signal as claimed in claim 55, further comprising the step of triggering said slowing step only when the amplitude of said ongoing EEG signal exceeds a first predetermined threshold level.

57. A method of producing a biofeedback signal as claimed in claim 56, further comprising the step of generating said sequence of notes over again when the amplitude of said ongoing EEG signal exceeds a second predetermined threshold level that is greater than said first predetermined threshold level.

58. A method of producing a biofeedback signal as claimed in claim 55, further comprising the step of generating said sequence of notes over again when the amplitude of said ongoing EEG signal exceeds a second predetermined threshold level that is greater than said first predetermined threshold level.

59. Music derived from brain waves by a process comprising the steps of:
receiving an ongoing EEG signal from at least one region of the brain of a biological entity, said at least one region of the brain responding to acoustical stimulation, said ongoing EEG signal exhibiting semiperiodic, moment-by-moment change;
generating an acoustical indication of the moment-by-moment change of said ongoing EEG signal;
adding musical flavor to said acoustical indication;
directing said acoustical indication so as to be received by the brain; and
delaying said step of directing said acoustical indication for a period of time determined so that the brain responds to said acoustical indication with a predetermined phase relationship with respect to the ongoing EEG signal received from said region of the brain.

60. A brain wave driven cybernetic interface circuit adapted for cooperation with a nervous system, a brain, and an acoustical sensory organ, comprising:
means for selecting a predetermined form of electrical activity from the nervous system, said brain producing produce said electrical activity, said acoustical sensory organ adapted to respond to acoustical impulses, including
means for receiving an ongoing EEG signal from a region of the brain, and
means for filtering said ongoing EEG signal to select a particular type of neuroelectrical activity in the brain, said neuroelectrical activity exhibiting semiperiodic change;
means for reinforcing said neuroelectrical activity in the brain, including
means for generating an acoustical indication of said semiperiodic change,
means for adding musical flavor to said acoustical indication to form a musical feedback signal,
means for converting said musical feedback signal into acoustical impulses comprising feedback music,
means for directing said feedback music to be received by said acoustical sensory organ, and
means for delaying said directing means for a period of time determined so that the brain response to said feedback music occurs with a predetermined phase relationship with respect to the ongoing EEG signal received from said region of the brain; and
means for generating a control signal in response to a predetermined musical pattern in said feedback music.

61. A brain wave driven cybernetic interface circuit as claimed in claim 60, further comprising a musical instrument to receive said control signal and generate music in response thereto.

62. A method of forming a cybernetic interface, comprising the steps of:
selecting a predetermined form of electrical activity from a nervous system, said nervous system having a brain to produce said electrical activity and an acoustical sensory organ to respond to acoustical impulses, including the steps of
receiving an ongoing EEG signal from a region of the brain, and
filtering said ongoing EEG signal to select a particular type of neuroelectrical activity in the brain, said neuroelectrical activity exhibiting semiperiodic change;
reinforcing said neuroelectrical activity in the brain including the steps of
generating an acoustical indication of said semiperiodic change,
adding musical flavor to said acoustical indication to form a musical feedback signal,
converting said musical feedback signal into acoustical impulses comprising feedback music,
directing said feedback music to be received by said acoustical sensory organ, and
delaying said step of directing for a period of time determined so that the brain responds to said feedback music with a predetermined phase relationship with respect to the ongoing EEG signal received from said region of the brain; and
generating a control signal in response to a predetermined musical pattern in said feedback music.

63. A method of forming a cybernetic interface as claimed in claim 62, further comprising the step of directing said control signal to a musical instrument that generates music in response thereto.

64. A method of forming a cybernetic interface as claimed in claim 62, wherein said nervous system is a human nervous system.

65. A neural stimulation apparatus, comprising:
means for noninvasively extracting an ongoing EEG signal from a predetermined region of a brain;
means for converting said EEG signal into music, said music having physiological information and musical flavor;
means for directing said music to an auditory sensory organ of said brain; and
means for delaying said directing means for a period of time determined so that said response of said region of the brain said music occurs with a predetermined phase relationship with respect to the ongoing EEG signal extracted from said region of the brain.

66. A neural stimulation apparatus as claimed in claim 65, wherein said noninvasive extraction means comprises a magnetometer.

67. A neural stimulation apparatus as claimed in claim 66, wherein said magnetometer comprises means for triangulating EEG activity occurring within said brain.

68. A method of stimulating neural activity, comprising the steps of:
noninvasively extracting an ongoing EEG signal from a predetermined region of a brain;
converting said EEG signal into music, said music having physiological information and musical flavor;
directing said music to an auditory sensory organ of said brain; and
delaying said directing step for a period of time determined so that said region of the brain responds to said music with a predetermined phase relationship with respect to the ongoing EEG signal extracted from said region of the brain.

69. A method of stimulating neural activity as claimed in claim 68, wherein said step of extracting said ongoing EEG signal comprises the step of detecting semiperiodic changes in magnetic field indicative of said ongoing EEG activity.

70. A method of stimulating neural activity as claimed in claim 69, wherein said step of detecting semiperiodic changes in magnetic field comprises the step of triangulating said ongoing EEG activity so as to extract only ongoing EEG activity from a well defined region of said brain.

71. A method of stimulating neural activity as claimed in claim 70, wherein said brain is a human brain.

* * * * *

UNITED STATES PATENT AND TRADEMARK OFFICE
CERTIFICATE OF CORRECTION

PATENT NO. : 4,883,067

DATED : Nov. 28, 1989

INVENTOR(S) : Geoffrey Wright and Joel Knispel

It is certified that error appears in the above-identified patent and that said Letters Patent is hereby corrected as shown below:

On the title page the inventors should appear as follows:
 [19] "Knispel et al" should read --Wright et al --.

[75] Geoffrey Wright, Baltimore; Joel Knispel, Timoninum, both of Md.

Column 29:
 In Claim 60, line 31, delete, "produce".

Column 30:
 In Claim 65, line 43, after "brain" insert --to--.

Signed and Sealed this

Sixth Day of October, 1992

*Attest:*

DOUGLAS B. COMER

*Attesting Officer*      *Acting Commissioner of Patents and Trademarks*